US008999382B2

(12) United States Patent
Aleksov et al.

(10) Patent No.: US 8,999,382 B2
(45) Date of Patent: Apr. 7, 2015

(54) DRUG DELIVERY SYSTEM FOR ADMINISTRATION OF POORLY WATER SOLUBLE PHARMACEUTICALLY ACTIVE SUBSTANCES

(75) Inventors: Julian Aleksov, Lidingö (SE); Igor Lokot, Uppsala (SE)

(73) Assignee: Ardenia Investments, Ltd., London, Greater London (GB)

( * ) Notice: Subject to any disclaimer, the term of this patent is extended or adjusted under 35 U.S.C. 154(b) by 506 days.

(21) Appl. No.: 12/809,252

(22) PCT Filed: Dec. 18, 2008

(86) PCT No.: PCT/SE2008/051515
§ 371 (c)(1),
(2), (4) Date: Sep. 15, 2010

(87) PCT Pub. No.: WO2009/078802
PCT Pub. Date: Jun. 25, 2009

(65) Prior Publication Data
US 2011/0014281 A1 Jan. 20, 2011

(30) Foreign Application Priority Data
Dec. 19, 2007 (WO) .................. PCT/SE2007/001127

(51) Int. Cl.
| A61K 9/48 | (2006.01) |
| A61K 39/00 | (2006.01) |
| A61K 9/20 | (2006.01) |
| A61K 31/185 | (2006.01) |
| A61K 9/51 | (2006.01) |
| A61K 9/14 | (2006.01) |
| A61K 31/337 | (2006.01) |

(52) U.S. Cl.
CPC ............... *A61K 9/5123* (2013.01); *A61K 9/145* (2013.01); *A61K 31/337* (2013.01)

(58) Field of Classification Search
None
See application file for complete search history.

(56) References Cited

U.S. PATENT DOCUMENTS

| 6,197,809 B1 | 3/2001 | Strelchenok |
| 2004/0048923 A1 | 3/2004 | Strelchenok et al. |
| 2005/0191359 A1 | 9/2005 | Goldshtein et al. |
| 2007/0082838 A1 | 4/2007 | De et al. |

FOREIGN PATENT DOCUMENTS

| EP | 1 666 031 A1 | 6/2006 |
| WO | 01/17546 | 3/2001 |
| WO | 02/092600 | 11/2002 |
| WO | 2005/089106 | 9/2005 |
| WO | 2006/017246 A2 | 2/2006 |
| WO | 2006/106519 | 10/2006 |
| WO | 2007/001356 | 1/2007 |
| WO | 2009/078803 | 6/2009 |
| WO | 2009/078804 | 6/2009 |

OTHER PUBLICATIONS

NPL website: Aerosols & Particulate Matter (www.mfg.mtu.edu/cyberman/environment/air/pmintro.html); downloaded Feb. 23, 2014.*
Saadia Hassan et al., "Cytotoxic activity of a new paclitaxel formulation, Pacliex, in vitro and in vivo", Cancer Chemother Pharmacol, 2005, vol. 55, pp. 47-54 (Previously identified in Information Disclosure Statement filed on Jun. 18, 2010, copy now provided).
D. V. Arsenov et al., "Synthesis of N-(all-transretinoyl)doxorubicin and study of the antitumor activity of its complex with blood serum proteins", Pharmaceutical Chemistry Journal, 2001, vol. 35, No. 4, pp. 186-189 (Previously identified in Information Disclosure Statement filed on Jun. 18, 2010, copy now provided).
Mahesh Chavanpatil et al., "Polymer-Surfactant Nanoparticles for Sustained Release of Water-Soluble Drugs", Journal of Pharmaceutical Sciences, Dec. 2007, vol. 96, No. 12 pp. 3379-3389 (Previously identified in Information Disclosure Statement filed on Jun. 18, 2010, copy now provided).
Torchilin, "Micellar Nanocarriers: Pharmaceutical Perspectives", Pharmaceutical Research, vol. 24, No. 1, Jan. 2007, pp. 1-16.
Saadia Hassan et al., "Cytotoxic activity of a new paclitaxel formulation, Pacliex, in vitro and in vivo", Cancer Chemother Pharmacol, 2005, vol. 55, pp. 47-54 (copy to be provided).
D. V. Arsenov et al., "Synthesis of N-(all-transretinoyl)doxorubicin and study of the antitumor activity of its complex with blood serum proteins", Pharmaceutical Chemistry Journal, 2001, vol. 35, No. 4, pp. 186-189 (copy to be provided).
Mahesh Chavanpatil et al., "Polymer-Surfactant Nanoparticles for Sustained Release of Water-Soluble Drugs", Journal of Pharmaceutical Sciences, Dec. 2007, vol. 96, No. 12 pp. 3379-3389 (copy to be provided).
International Search Report for corresponding International Application No. PCT/SE2008/051515 mailed Mar. 20, 2009.
Written Opinion for corresponding International Application No. PCT/SE2008/051515 mailed Mar. 20, 2009.
(Continued)

*Primary Examiner* — Jeffrey T Palenik
(74) *Attorney, Agent, or Firm* — Renner, Otto, Boisselle & Sklar, LLP

(57) ABSTRACT

This invention relates to a drug delivery system for administration of poorly water soluble pharmaceutically active substance, a pharmaceutical composition comprising such a drug delivery system, and a method for the preparation of such a drug delivery system. The invention also relates to a method for controlling the particle size and/or particle shape and/or particle size distribution in such a drug delivery system, and to a method for increasing the drug loading capacity of the particles. Furthermore the invention also relates to the use of such a drug delivery system for the preparation of a medicament for the treatment of cancer.

7 Claims, 6 Drawing Sheets

(56) References Cited

OTHER PUBLICATIONS

Written Opinion of the International Preliminary Examining Authority for corresponding International Application No. PCT/SE2008/051515 mailed Nov. 20, 2009.
International Preliminary Report on Patentability for corresponding International Application No. PCT/SE2008/051515 mailed Oct. 19, 2009.
International Search Report for corresponding International Application No. PCT/SE2008/051516 mailed Mar. 20, 2009.
Written Opinion for corresponding International Application No. PCT/SE2008/051516 mailed Mar. 20, 2009.
Written Opinion of the International Preliminary Examining Authority for corresponding International Application No. PCT/SE2008/051516 mailed Nov. 20, 2009.
International Preliminary Report on Patentability for corresponding International Application No. PCT/SE2008/051516 mailed Mar. 25, 2010.
International Search Report for corresponding International Application No. PCT/SE2008/051517 mailed Mar. 20, 2009.
Written Opinion for corresponding International Application No. PCT/SE2008/051517 mailed Mar. 20, 2009.
PCT Communication in Cases for Which No Other Form Is Suitable—Corrected International Search Report and Written Opinion for corresponding International Application No. PCT/SE2008/051517 mailed Apr. 1, 2009.
Written Opinion of the International Preliminary Examining Authority for corresponding International Application No. PCT/SE2008/051517 mailed Nov. 20, 2009.
International Preliminary Report on Patentability for corresponding International Application No. PCT/SE2008/051517 mailed Mar. 25, 2010.
Office Action issued Jun. 25, 2013 in the copending Japanese Patent Application No. 2010-539386.

* cited by examiner

DRUG DELIVERY SYSTEM FOR ADMINISTRATION OF POORLY WATER SOLUBLE PHARMACEUTICALLY ACTIVE SUBSTANCES

This application is a national phase of International Application No. PCT/SE2008/051515 filed Dec. 18, 2008 and published in the English language, which claims priority to International Application No. PCT/SE2007/001127 filed Dec. 19, 2007.

FIELD OF THE INVENTION

This invention relates to a drug delivery system for administration of poorly water soluble pharmaceutically active substances, a pharmaceutical composition comprising such a drug delivery system, and a method for the preparation of such a drug delivery system. The invention also relates to a method for controlling the particle size and/or particle shape and/or particle size distribution in such a drug delivery system, and to a method for increasing the drug loading capacity of the particles. Furthermore the invention also relates to the use of such a drug delivery system for the preparation of a medicament for the treatment of cancer.

BACKGROUND OF THE INVENTION

There is a critical need in the pharmaceutical and other related industries to formulate industrially useful water-insoluble or poorly water soluble substances into formulations for oral, injectable, inhalation, ophthalmic, and other routes of delivery. Industrially useful water insoluble or poorly water soluble substances include water insoluble or poorly water soluble biologically useful compounds, imaging agents, pharmaceutically useful compounds and in particular water insoluble and poorly water soluble drugs for human and veterinary medicine.

No limitation is imposed on the kind of water-insoluble or poorly water soluble substances for use in the present invention. Examples include antipyretics, anti-inflammatories, analgesics, ataractics, sedatives, antitumor agents, antimicrobials, antibiotics, antilipemics, antitussives/expectorants, muscle relaxants, antiepileptics, antiulcers, antidepressants, antiallergics, cardiotonics, antiarrhythmics, vasodilators, hypotensors/diuretics, diabetes therapeutics, tuberculostatics, antirheumatics, steroids, narcotic antagonists, hormones, fat-soluble vitamins, anticoagulants, ischemic disease therapeutics, immune disease therapeutics, Alzheimer's disease therapeutics, osteoporosis therapeutics, angiopoiesis therapeutics, retinosis therapeutics, retinal vein occlusion therapeutics, senile disciform macular degeneration, cerebrovascular spasm therapeutics, cerebral thrombosis therapeutics, cerebral infarction therapeutics, cerebral occlusion therapeutics, intracerebral hemorrhage therapeutics, subarachnoid hemorrhage therapeutics, hypertensive encephalopathy therapeutics, transient cerebral ischemic attack therapeutics, multi-infarct dementia therapeutics, arterial sclerosis therapeutics, Huntington's disease therapeutics, brain tissue disorder therapeutics, optic neuropathy therapeutics, glaucoma therapeutics, ocular hypertension therapeutics, retinal detachment therapeutics, arthritis therapeutics, antisepsis drugs, antiseptic shock drugs, antiasthma drugs, pollakiuria/incontinentia therapeutics, atopic rhinitis therapeutics, allergic rhinitis therapeutics, cosmetic compositions, agrichemical compositions, insecticides, bactericides, herbicides, beverage or food compositions, immunosuppressants and animal drug compositions.

The fact that only water soluble substances can be administrated intravenously considerably impoverishes the assortment of organic molecules that can be used as antineoplastic drugs, as many if not most of these are poorly water soluble.

Incorporation of polar functions into such substances does not solve this problem because the changes of the structure lead to loss of the relevant pharmacological properties of the drugs.

Development of drug delivery systems which could enable dissolvation of poorly soluble compounds in aqueous solutions would be hugely instrumental in the efforts of realizing the anticancer potential of a vast number of substances, and would provide for creation of novel generations of drugs.

Paclitaxel and docetaxel belong to the taxane class of anticancer drugs because they or their precursors are produced by the plants of the genus *Taxus* (yews). Paclitaxel is still produced by isolation from natural sources while docetaxel, a semi-synthetic analogue of paclitaxel, is synthesized from 10-deacetyl baccatin. Paclitaxel differs from docetaxel by an acetylated hydroxyl function at position 10 and a benzoyl moiety instead of tert-butyl on the phenylpropionate side chain. The mechanism of action of taxanes is based on their ability to bind to the β subunit of tubulin which interferes with the depolymerization of microtubules, thereby damaging dividing cells. This specificity of action is widely used in oncology to treat different solid tumors, especially ovarian, lung, breast, bladder, head and neck cancer.

Paclitaxel and docetaxel have poor oral bioavailability and therefore intravenous (i.v.) infusion is the only way of administration. Scarce water solubility also makes it impossible to use aqueous solutions of these taxanes. Several delivery vehicles have been applied to solve this problem.

TAXOL® is based on the ability of CREMOPHOR® EL, a polyethoxylated castor oil, to dissolve paclitaxel in the weight-to-weight (w/w) ratio 87:1. It is chronologically the first commercial taxane formulation which has opened the era of taxane use in oncology. However it was later found that CREMOPHOR® is the cause of hypersensitivity reactions during TAXOL® infusion and for minimization of the incidence and severity of these reactions a premedication with histamine blockers and glucocorticoids as well as continuous infusion schedules became standard practice.

In a second delivery system called TAXOTERE®, Polysorbate 80 (known under the trademark TWEEN® 80), a derivative of polyethoxylated sorbitol and oleic acid, plays the role of vehicle. In this case the w/w ratio is 24:1. Like CREMOPHOR® EL, Polysorbate 80 is a non-ionic detergent build of polyethoxy chains and can also induce hypersensitivity reactions.

ABRAXANE®, a third delivery system, consists of paclitaxel nanoparticles stabilized by human serum albumin in the w/w ratio 9:1 with the mean diameter of nanoparticles being 130 nm. The absence of non-ionic surfactants simplifies the treatment as no premedication is necessary and the infusion time is shortened. On the other hand the ABRAXANE® formulation is less potent than TAXOL® because ABRAXANE® nanoparticles like other particles with the size more than 100 nm are a substrate for reticuloendothelial system. Another disadvantage of this drug delivery vehicle is that human serum albumin isolated from donor blood is used, which always carries a small but definite risk of transmission of viral diseases.

Finally, it has been found that paclitaxel and docetaxel can be dissolved in aqueous solutions of water-soluble derivatives of retinoic acid acting as anionic surfactants.

The uniqueness of the structure of these derivatives enables them to dissolve paclitaxel and docetaxel in the surprisingly low w/w ratio of 0.5:1.

Ixabepilone, (epothilone B analog) is very similar to taxanes in terms of mode of action and solubility in aqueous solutions. It is indicated for the treatment of metastatic or locally advanced breast cancer. Formulation of ixabepilone for IV administration, Ixempra, developed by BMS, like Taxol, is based on cremophor EL and therefore a premedication and prolonged infusion for the reducing of hypersensitivity reactions is required.

Etoposide, analog of toxin podophyllotoxin, is topoisomerase II inhibitor and is used for treatment of Ewing's sarcoma, lung cancer, testicular cancer, lymphoma and non-lymphocytic leukemia. Etoposide formulations for IV administration are based on PEG-derivatives such as Polysorbate 80 (TWEEN 80) or Macrogol 300 in order to solubilize the scarce water soluble active pharmaceutical ingredient.

Retinoids comprise a family of polyisoprenoids which includes vitamin A (retinol) and its natural (retinoic acid) and synthetic analogs (fenretinide, etretinate, tazarotene, bexarotene, adapalene). These compounds show a broad spectrum of biological activity including participation in control of cell proliferation, cell differentiation and embryonic development which enables to use retinoids as antineoplastic agents for treatment of different types of cancer such as leukemia, lymphoma, Kaposi's sarcoma, lung cancer and breast cancer. These compounds are also used for treatment of different skin disease like psoriasis, acne, and sun damaged skin. Retinoids are usually highly lipophilic compounds and their usage in form of aqueous solution demands application of some delivery system. However so far there are no any commercially developed water-soluble formulations of retinoids and they are available exclusively for oral administration.

Ciclosporin, sirolimus, tacrolimus, and everolimus are immunosuppressants which are scarcely water soluble. Bioavailability of the drugs at oral administration is only about 20%. Commercially available formulations of these immunosuppressants are based solely on the use of polyoxyethylated castor oil, which causes hypersensitivity reactions when intravenously administered.

Ciclosporin, cyclosporine, or cyclosporin, is an immunosuppressant drug widely used in post-allogeneic organ transplant to reduce the activity of a patient's immune system and so the risk of organ rejection. It has been studied in transplants of skin, heart, kidney, liver, lung, pancreas, bone marrow and small intestine. Initially isolated from a Norwegian soil sample, Ciclosporin A, the main form of the drug, is a cyclic nonribosomal peptide of 11 amino acids (an undecapeptide) produced by the fungus *Tolypocladium inflatum* Gams, and contains D-amino acids, which are rarely encountered in nature.

The search for and development of new drug delivery systems has increased with the realization of the fact that drugs in too high concentrations are toxic and—in best case—inactive in too low concentrations; however, exposing a cell to a too low concentrations of drugs often activates mechanisms of resistance to the drug. The range of concentrations where the drug elicits the desired response with less side-effects is known as "the therapeutic window".

Prolonged infusions have been proven to reduce the toxicity of anticancer agents but this mode of administration is significantly more complicated from a practical point of view.

It has been found that slow drug release can be achieved by using drugs that are bound or encapsulated in nanoparticles of different kind. These particles can circulate in blood for several days playing the role of "depots". The drug release occurs by diffusion of the encapsulated drugs or by erosion and decomposition of the particles. The most popular types of nanoparticles in this field of research are micelles and liposomes as the formation of such nanoparticles is a quite simple entropy driven process, i.e. they emerge spontaneously and their properties are programmed by conditions of the formation. The size of particles used in these delivery systems is within the range of 8 to 200 nm and even higher.

However, with the increase of the size, a particle becomes "visible" to the reticulo-endothelial system, a part of the immune system consisting of the phagocytic cells located in reticular connective tissue of lymph nodes, liver and spleen. The extent of reticulo-endothelial system clearance increases with the size of the particles, significantly reducing the total amount of the drug in the blood flow.

Another intriguing challenge in the field of drug delivery is the targeting of drugs to effect compartments which could increase the therapeutic effectiveness up to ultimate levels. Nanoparticles have been found very useful in this regard. Solid tumors differ pathoanatomically from healthy tissues by an extensive angiogenesis, as well as a hyperpermeable and defective vasculature architecture. In other words the size of the tumour capillaries is larger, making it potentially possible to significantly increase the passive transport of nanoparticles loaded with cytotoxic cargo to the tumour in comparison to a healthy endothelium.

US 2004048923 describes a group of retinoids including among numerous others the sodium salt of N-(all-trans-retinoyl)-L-cysteic acid methyl ester and the sodium salt of N-(13-cis-retinoyl)-L-cysteic acid methyl ester. It is stated that the substances make it possible to manufacture new micelle formulations of poorly soluble pharmaceutical compounds like paclitaxel and docetaxel.

WO 02092600 relates to a method for preparing a water-soluble formulation of paclitaxel, comprising the steps of dissolving paclitaxel in a first solvent, dissolving a compound chosen among N-(all-trans-Retinoyl)-L-cysteic acid, N-(13-cis-Retinoyl)-L-cysteic acid, N-(all-trans-Retinoyl)-L-homocysteic acid, N-(13-cis-Retinoyl)-L-homocysteic acid, N-(all-trans-Retinoyl)-L-cysteinesulfinic acid, and N-(13-cis-Retinoyl)-L-cysteinesulfinic acid in a second solvent, mixing the aliquots of the resulting solutions of paclitaxel and the said compound in a desired molar ratio, and evaporating the resulting mixture to dryness.

Although the poor solubility of the pharmaceutical compounds may suggest that they are in particular form, US 2004048923 and WO 02092600 are both completely silent regarding the size and the morphology of the particles. There is in particular no indication or suggestion that they should be in amorphous state, or even that they could exist in such a state. Little less is any way of providing particles in such a state disclosed. As well known to those skilled in the polymorphism, including possible amorphism, is basically unpredictable for organic substances.

SHORT SUMMARY OF THE INVENTION

The creation of a new drug delivery system with controlled or in advance programmed drug release mimicking prolonged administrations would be greatly desired.

One object of the present invention is to provide such a drug delivery system.

Thus, one aspect of the invention relates to a drug delivery system for administration of at least one pharmaceutically active substance having a solubility per se in water of less than about 100 µg/ml, said substance being in particulate form with an effective average particle size of less than about 100 nm, wherein the substance particles are essentially amorphous; the substance particles are entrapped in nanoparticles formed of a sodium salt of the methyl ester of N-all-trans-retinoyl cysteic acid, a sodium salt of the methyl ester of N-13-cis-retinoyl cysteic acid, or a combination thereof; and the weight-to-weight ratio of said sodium salt of the methyl ester of N-all-trans-retinoyl cysteic acid, sodium salt of the methyl ester of N-13-cis-retinoyl cysteic acid, or combination thereof, to said substance is in the range from 0.5:1 to 20:1.

BRIEF DESCRIPTION OF THE DRAWINGS

The present invention will be described in closer detail in the following description, examples and attached drawings, in which.

DESCRIPTION OF EMBODIMENTS OF THE INVENTION

Figure 1:
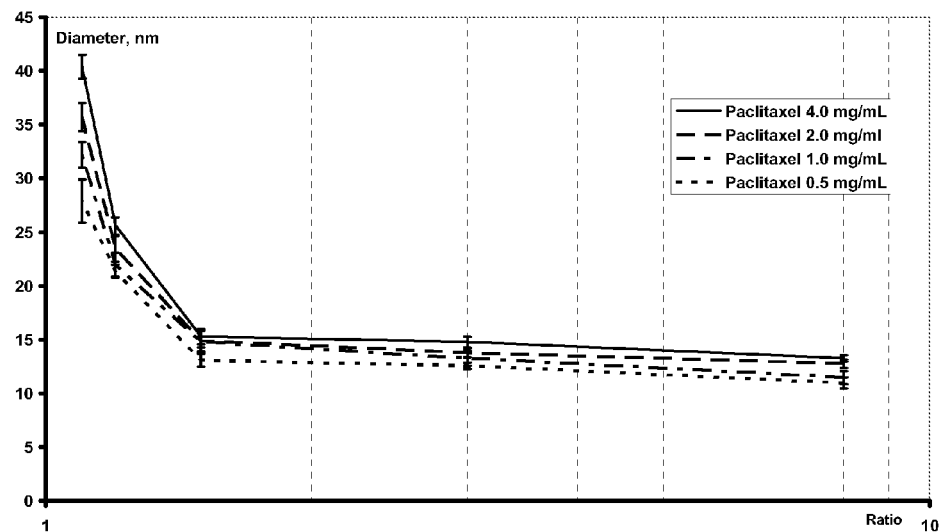
FIG. 1 shows the dependence of the particle size on the w/w ratio of sodium salt of methyl ester of N-all-trans-retinoyl cysteic acid to paclitaxel at different paclitaxel concentrations in an aqueous solution of sodium chloride at a concentration of 9 mg/ml.

Before the present invention is disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the claims, the singular forms "a", "an", and "the" include plural referents unless the context clearly dictates otherwise.

In this specification, unless otherwise stated, the term "about" modifying the quantity of an ingredient in the drug delivery systems or compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the drug delivery systems or compositions or carry out the methods; and the like. The term "about" also encompasses amounts that differ due to different equilibrium conditions for a composition resulting from a particular initial mixture. Whether or not modified by the term "about", the claims include equivalents to the quantities.

In this specification, unless otherwise stated, the term "drug delivery system" refers to a formulation or device that delivers therapeutic agent(s) to desired body location(s) and/or provides timely release of therapeutic agent(s).

In this specification, unless otherwise stated, the term "particle size" refers to the Z-average diameter as measured by dynamic light scattering with the use of red laser with a wavelength of 633 nm. By "an effective average particle size of less than about 100 nm" it is meant that at least 90% of the particles have a size of less than about 100 nm when measured by the above-noted technique.

In this specification, unless otherwise stated, the term "nanoparticle" refers to a microscopic particle whose size is measured in nanometers. Nanoparticles of the invention typically range from about 1 to about 999 nm in diameter, and can include an entrapped, encapsulated, or enclosed biologically active molecule.

In this specification, unless otherwise stated, the term "solubility" of a substance refers to the ability of that substance to be dissolved in a specified solvent at about room temperature, by which is meant from between about 15° C. to about 38° C.

In this specification, unless otherwise stated, the term "amorphous" is intended to indicate a solid structure that is either non-crystalline or consists of very small crystals having a particle size of about 10 nm or less.

In this specification, unless otherwise stated, the term "cytotoxic compound" refers to a compound that has the ability of arresting the growth of, or killing, cells.

In this specification, unless otherwise stated, the term "cytostatic compound" refers to a compound that has the ability of bringing cells, although not necessarily lysed or killed, into a permanent non-proliferative state.

In this specification, unless otherwise stated, the term "immunosuppressant" refers to a compound that has the ability of inhibiting the activity of the immune system, in particular for preventing rejection of a transplant organ and in disorders where the body's immune system attacks its own tissues In this specification, unless otherwise stated, the term "derivative" refers to a compound formed from the original structure either directly, by chemical reaction of the original structure, or by a "modification" which is a partial substitution of the original structure, or by design and de novo synthesis. Derivatives may be synthetic, or may be metabolic products of a cell or an in vitro enzymatic reaction.

In one embodiment the substance particles in the inventive drug delivery system have an effective average particle size of less than about 50 nm.

In another embodiment the substance particles in the inventive drug delivery system have an effective average particle size in the range of about 5-50 nm.

In yet another embodiment the substance particles in the inventive drug delivery system have an effective average particle size in the range of about 8-30 nm.

In one embodiment of the present invention the weight-to-weight ratio of the sodium salt of methyl ester of N-all-trans-retinoyl cysteic acid, sodium salt of methyl ester of N-13-cis-retinoyl cysteic acid, or combination thereof, to the pharmaceutically active substance is in the range from about 1:1 to about to 10:1.

In one embodiment of the present invention the pharmaceutically active substance is a cytotoxic or a cytostatic compound; in one aspect of this embodiment the cytotoxic or cytostatic compound is bischloronitrosourea (Carmustine); in another aspect of this embodiment the cytotoxic or cytostatic compound is etoposide; in yet another aspect of this embodiment the cytotoxic or cytostatic compound is a taxane, and in a more specific aspect the taxane is chosen among paclitaxel, docetaxel, and derivatives thereof. In another specific aspect of said embodiment the invention relates to such a drug delivery system for use in treatment of cancer.

In one embodiment of the present invention the pharmaceutically active substance is an immunosuppressant; in one aspect of this embodiment the immunosuppressant is chosen among ciclosporin, sirolimus, tacrolimus and derivatives thereof. In another aspect of said embodiment the invention relates to such a drug delivery system for use in post-allogeneic organ transplant.

Another embodiment of the invention relates to a pharmaceutical composition comprising a pharmaceutically acceptable carrier and a drug delivery system of this kind. In one aspect of this embodiment the pharmaceutically active substance is a cytotoxic or a cytostatic compound; in one aspect of this embodiment the cytotoxic or cytostatic compound is bischloronitrosourea (Carmustine); in another aspect of this embodiment the cytotoxic or cytostatic compound is etoposide; in yet another aspect of this embodiment the compound is a taxane, which may be chosen among paclitaxel, docetaxel, and derivatives thereof; in another aspect of this embodiment of the present invention the pharmaceutically active substance is an immunosuppressant; in one aspect of this embodiment the immunosuppressant is chosen among ciclosporin, sirolimus, tacrolimus and derivatives thereof. In one aspect of this embodiment the pharmaceutical composition may be provided in the form of an aqueous solution, a gel, a cream, an ointment, a tablet, a capsule, or a softgel.

A further embodiment of the invention relates to the use of a sodium salt of the methyl ester of N-all-trans-retinoyl cysteic acid, a sodium salt of the methyl ester of N-13-cis-retinoyl cysteic acid, or a combination thereof, in the preparation of such a drug delivery system.

Yet another embodiment of the invention relates to a method for the preparation of a drug delivery system comprising nanoparticles formed of a sodium salt of the methyl ester of N-all-trans-retinoyl cysteic acid, a sodium salt of the methyl ester of N-13-cis-retinoyl cysteic acid, or a combination thereof, and at least one pharmaceutically active substance having a solubility per se in water of less than about 100 µg/ml, wherein said substance is provided in the form of essentially amorphous particles with an effective average particle size of less than about 100 nm; the size of said nanoparticles is controlled to have an effective average particle size of less than about 100 nm by adjusting the weight-to-weight ratio of said sodium salt of the methyl ester of N-all-trans-retinoyl cysteic acid, sodium salt of the methyl ester of N-13-cis-retinoyl cysteic acid, or combination thereof, to said substance to be in the range from about 0.5:1 to about 20:1. The present invention also provides a drug delivery system obtainable by this method as well as a pharmaceutical composition comprising a pharmaceutically acceptable carrier and such a drug delivery system.

A yet further embodiment of the invention relates to a method for controlling the particle size and/or particle shape and/or particle size distribution of nanoparticles formed of a sodium salt of the methyl ester of N-all-trans-retinoyl cysteic acid, a sodium salt of the methyl ester of N-13-cis-retinoyl cysteic acid, or a combination thereof, and at least one pharmaceutically active substance having a solubility per se in water of less than about 100 µg/ml in a process for the preparation of a drug delivery system, wherein said substance is provided in the form of essentially amorphous particles with an effective average particle size of less than about 100 nm; the particle size and/or particle shape and/or particle size distribution of said nanoparticles is controlled by adjusting the weight-to-weight ratio of said sodium salt of the methyl ester of N-all-trans-retinoyl cysteic acid, sodium salt of the methyl ester of N-13-cis-retinoyl cysteic acid, or combination thereof, to said substance to be in the range from about 0.5:1 to about 20:1. In one aspect of this embodiment the size of the nanoparticles is controlled to be in the range of about 10-100 nm.

Yet another embodiment of the invention relates to a method for controlling the particle size of nanoparticles formed of a sodium salt of the methyl ester of N-all-trans-retinoyl cysteic acid, a sodium salt of the methyl ester of N-13-cis-retinoyl cysteic acid, or a combination thereof, and at least one pharmaceutically active substance having a solubility per se in water of less than about 100 µg/ml in a process for the preparation of a drug delivery system, wherein said substance is provided in the form of essentially amorphous particles with an effective average particle size of less than about 100 nm; said essentially amorphous particles are submitted into and/or produced in an aqueous solution containing at least one ionized salt, said aqueous solution having an ionic strength I; and the particle size of the nanoparticles is increased by increasing I or decreased by decreasing I.

In one aspect of this embodiment the pharmaceutically active substance is a taxane and said at least one ionized salt is sodium chloride. This is useful for the production of i.v. infusion solutions as sodium and chloride ions are the most abundant ions in the human body and also in the bodies of many animals.

In another aspect of this embodiment of this embodiment the ionized salt comprises polyvalent cations, such as, for instance, double valenced cations. Such cations do not only increase the ionic strength of the solvent in general, thereby increasing the particle size, but also stabilize the particles formed.

The use of taxane-containing particles having a size within the range of about 10-100 nm significantly improves the therapeutic efficacy of these anti-cancer compounds by extension a blood circulation of the drugs, lowering their reticulo-endothelial clearance and selective penetration of defective vasculature. Besides the advantages of the use of taxanes in the form of such nanoparticles in vivo, i.e. slow drug release and increased permeability of tumour vasculature, it has also been found that the activity of taxane formulations containing such nanoparticles is more expressed in vitro in different solid tumour cell lines. Moreover the cytotoxicity of these formulations dramatically depends on the particle size.

Another embodiment of the invention relates to a method for increasing the drug loading capacity of nanoparticles formed of a sodium salt of the methyl ester of N-all-trans-retinoyl cysteic acid, a sodium salt of the methyl ester of N-13-cis-retinoyl cysteic acid, or a combination thereof, and at least one pharmaceutically active substance having a solubility per se in water of less than about 100 µg/ml in a process for the preparation of a drug delivery system by providing said substance in the form of essentially amorphous particles with an effective average particle size of less than about 100 nm; and adjusting the weight-to-weight ratio of said sodium salt of the methyl ester of N-all-trans-retinoyl cysteic acid, sodium salt of the methyl ester of N-13-cis-retinoyl cysteic acid, or combination thereof, to said substance to be in the range from about 0.5:1 to about 20:1.

In each one of said inventive methods the pharmaceutically active substance may be provided in the form of essentially amorphous particles with an effective average particle size of less than about 100 nm by way of a method comprising the steps of: dissolving said substance in a suitable organic solvent to provide an organic solution of said substance; adding about 0.01-3 molar equivalents of a sodium salt of the methyl ester of N-all-trans-retinoyl cysteic acid, a sodium salt of the methyl ester of N-13-cis-retinoyl cysteic acid, or a combination thereof, to said organic solution; and evaporating said organic solvent from said organic solution to provide a residue which comprises the pharmaceutically active substance in the form of essentially amorphous particles. In one embodiment of this method about 0.1-1 molar equivalents of a sodium salt of the methyl ester of N-all-trans-retinoyl cysteic acid, a sodium salt of the methyl ester of N-13-cis-retinoyl cysteic acid, or a combination thereof, is added to the organic solution.

The proposed method is based on the ability of a sodium salt of the methyl ester of N-all-trans-retinoyl cysteic acid, as well as a sodium salt of the methyl ester of N-13-cis-retinoyl cysteic acid to prevent crystallization of pharmaceutically active substance such as, for instance, taxanes.

During the evaporation of the organic solvent the sodium salt of the methyl ester of N-all-trans-retinoyl cysteic acid, sodium salt of the methyl ester of N-13-cis-retinoyl cysteic acid, or combination thereof, co-crystallize with the pharmaceutically active substance, forming a film. Water added to this film dissolves the sodium salt of the methyl ester of N-all-trans-retinoyl cysteic acid, sodium salt of the methyl ester of N-13-cis-retinoyl cysteic acid, or combination thereof, and provides the pharmaceutically active substance in a highly amorphous form with tremendously increased surface area.

The thus obtained solution of essentially amorphous particles of the pharmaceutically active substance can be used directly without isolation or purification for infusions or for the manufacturing of freeze dried products for future reconstitutions.

Alternatively, the essentially amorphous particles of the pharmaceutically active substance can be provided in dry form by way of, for instance, evaporation, and then later on be dissolved in an aqueous solution comprising about 0.01-50 molar equivalents of said sodium salt of the methyl ester of N-all-trans-retinoyl cysteic acid, sodium salt of the methyl ester of N-13-cis-retinoyl cysteic acid, or combination thereof. In one embodiment said active substance particles may be dissolved in such a solution comprising about 0.1-5 molar equivalents of a sodium salt of the methyl ester of N-all-trans-retinoyl cysteic acid, a sodium salt of the methyl ester of N-13-cis-retinoyl cysteic acid, or combination thereof. The essentially amorphous particles are possible to dissolve in a solution of a sodium salt of the methyl ester of N-all-trans-retinoyl cysteic acid, a sodium salt of the methyl ester of N-13-cis-retinoyl cysteic acid, or combination thereof, within a couple of minutes.

In another alternative, a solution of the pharmaceutically active substance in an organic solvent is added to an aqueous solution of a sodium salt of the methyl ester of N-all-trans-retinoyl cysteic acid, a sodium salt of the methyl ester of N-13-cis-retinoyl cysteic acid, or a combination thereof, whereafter the organic solvent is evaporated, leaving an aqueous solution comprising the pharmaceutically active substance in an amorphous form.

This method can be optimized and simplified by arranging influx of organic solution of the pharmaceutically active substance into an evaporation flask containing an aqueous solution of a sodium salt of the methyl ester of N-all-trans-retinoyl cysteic acid, a sodium salt of the methyl ester of N-13-cis-retinoyl cysteic acid, or a combination thereof, simultaneously with evaporation.

The flow-rate of the organic solution, the internal pressure in the evaporation system as well as the evaporation temperature may be chosen in such a way that concentration of organic solution does not exceed 15%.

The organic solvent used in the process for providing the pharmaceutically active substance in the form of essentially amorphous particles may be an alcohol such as, for instance, methanol or ethanol. The use of methanol which has lower boiling point instead of ethanol simplifies the evaporation of the alcohol-water mixtures.

However, as residues of organic solvent may be less appropriate for direct in vivo application, the organic solutions of the essentially amorphous particles of pharmaceutically active substance may, for instance, be freeze-dried to remove the organic solvent, leaving the essentially amorphous particles of pharmaceutically active substance in a convenient powder form for storage and preparation of new formulations.

According to other embodiments of the present invention there is also provided:

the use of the inventive drug delivery system for the preparation of a medicament for the treatment of cancer, and to a method for the treatment of cancer wherein the inventive drug delivery system is administered in a therapeutically effective amount to a patient in need of such treatment; and the use of the inventive pharmaceutical composition for the preparation of a medicament for the treatment of cancer, and to a method for the treatment of cancer, wherein the inventive pharmaceutical composition is administered in a therapeutically effective amount to a patient in need of such treatment.

the use of the inventive drug delivery system for the preparation of a medicament for use in post-allogeneic organ transplant, and to a method for post-allogeneic organ transplant wherein the inventive drug delivery system is administered in a therapeutically effective amount to a patient in need of such treatment; and the use of the inventive pharmaceutical composition for the preparation of a medicament for use in post-allogeneic organ transplant, and to a method for post-allogeneic organ transplant, wherein the inventive pharmaceutical composition is administered in a therapeutically effective amount to a patient in need of such treatment.

The water soluble taxane formulations obtained with the use of a sodium salt of the methyl ester of N-all-trans-retinoyl cysteic acid, a sodium salt of the methyl ester of N-13-cis-retinoyl cysteic acid, or a combination thereof, are stable for several hours in the broad interval of conditions of formation of these formulations.

Thus, the present invention makes it possible to provide aqueous solutions of taxanes with otherwise poor water solubility, like paclitaxel and docetaxel, for infusion without any use of non-ionic surfactants. This significantly reduces hypersensitivity reaction against the infusion solutions, shortens the infusion time, and obviates the need of premedication of patients against such hypersensitivity.

The invention will be illustrated in closer detail in the following non-limiting examples.

EXAMPLES

Materials and Methods

Formulations of active pharmaceutical ingredients with a sodium salt of the methyl ester of N-all-trans-retinoyl cysteic acid, a sodium salt of the methyl ester of N-13-cis-retinoyl cysteic acid, or a combination thereof, were prepared by reconstitution of either freshly evaporated or freeze dried residues of an active ingredient with the retinoyl cysteic acid derivatives by a specified solution for reconstitution.

Paclitaxel, Ciclosporine A and all-trans-retinoic acid were purchased from Sigma-Aldrich Sweden AB. Docetaxel was purchased from ScinoPharm Taiwan, Ltd. Ixabepilone was purchased from Chemtronica KB, Sweden. Fenretinide was synthesized according to a standard procedure (Cancer Research, 39, 1339-1346, April 1979). Taxol, Taxotere and Abraxane were purchased from pharmacy stores and reconstituted according to manufacturers prescribing information.

Particle size of formulations was measured by dynamic light scattering method with the use of a red laser (633 nm). Zeta(Z)-potential was measured by electrophoretic light scattering method. Nano-ZS (Malvern Instruments Ltd.) was used for determination both particle size and zeta-potential. Average values of three independent measurements were calculated for plotting of particle size and zeta-potential behaviour. Y-error bars are composed by +/− standard deviation of the measurements.

For evaluation of cytotoxicity in vitro the cells of different human tumour cell lines were purchased from American Type Culture Collection (Rockville, Md., USA): Human Breast Adenocarcinoma Cell Line MDA-MB-231 (ATCC-HTB-26, Lot 3576799), Human Ovary Adenocarcinoma Cell Line SKOV-3 (ATCC-HTB-77, Lot 3038337) and Human Lung Non-Small Cancer Cell Line A549 (ATCC-CCL-185, Lot 3244171). MDA-MB-231 cells were propagated in MEM culture medium with 2 mM L-glutamine, 10% fetal bovine serum (FBS) and antibiotics. SKOV-3 cells were cultured in McCoy's 5A culture medium, supplemented with 1,5 mM L-glutamine, 10% FBS and antibiotics. All media and supplements were purchased from Sigma-Aldrich Co. (St. Louis, Mi., USA). Cell propagation of all lines was carried out in BD Falcon™ 25 or 75 cm² cultivation flasks (Becton Dickinson Labware). A549 cells were cultured in Ham's F-12 culture medium with 1 mM L-glutamine, 10% FBS and antibiotics. Cell propagation of all lines was carried out in BD Falcon™ 25 or 75 cm² cultivation flasks.

Drug cytotoxicity testing was carried out using BD Falcon™ 96-well cultivation plates for adherent cells (Becton Dickinson Labware). These plates were seeded by cells at $8\times10^3$ cells/well for MDA-MB-231, at $10\times10^3$ cells/well for SKOV-3 or at $6\times10^3$ cells/well for A549 in a volume of 200 µl/well. Both flasks and cultivation plates were incubated for cell growth at 37° C. in a humidified atmosphere of 95% air and 5% $CO_2$.

The cell cultures in the cultivation plates were allowed to adhere for 24 hour of incubation. On day 1 after cell seeding 4 µL solutions of the formulations to be tested with different concentrations in appropriate solvents were added to wells with cultures (dose—response experiments). In the control cultures 4 µL of the solvents were added as solvent control. The cells were incubated within 2-4 consecutive days. At the end of the incubation period adherent cells were detached by trypsinization and the number of viable cells was counted using trypan blue exclusion test and a hemocytometer. All experiment were performed at least three times and data were derived from an average of three determinations each in four replicates. The results were expressed as mean cell number±SE and the differences between control and test series evaluated by means of Student's t-test. The drug cytotoxicity was evaluated based on the extent of cell growth inhibition. The cell growth inhibition by the tested drugs was calculated as follows:

$$\text{Cell growth inhibition \%} = \frac{\text{Control} - \text{Test Series}}{\text{Control}} \times 100$$

In control series 4 µL of different solvents used for drug testing were added to cultures as negative solvent controls. The differences between these control series were insignificant; therefore an average of negative controls was applied for calculations.

Solutions of paclitaxel and docetaxel as well as their commercial formulations were used as positive controls. The differences in growth inhibition by these drugs in different solvents were insignificant; therefore an average inhibition of positive controls was applied for calculations.

The mean $IC_{50}\pm SE$ was calculated on the bases of at least three separate experiments.

Enhancement factors (EF) were calculated by dividing of $IC_{50}$ of the control comparison drug with $IC_{50}$ of the inventive formulation.

The ionic strength of a solution is a function of the concentration of all ions present in a solution.

$$I_c = \frac{1}{2}\sum_{B=1}^{n} c_B z_B^2$$

where $c_B$ is the concentration of ion B, $z_B$ is the charge number of that ion, and the sum is taken over all ions in the solution.

Example 1

Preparation of Amorphous Paclitaxel 12 ml of a paclitaxel stock solution in methanol (c=2.5 mg/ml) and 2 ml of an aqueous solution of a sodium salt of the methyl ester of N-all-trans-retinoyl cysteic acid (c=15 mg/ml) were evaporated in vacuo to dryness in a 50 ml round bottom flask. 15 ml of methanol was added to the flask and the residue was dissolved. The obtained solution was evaporated to dryness. The film obtained after the evaporation consisted of a mixture of amorphous paclitaxel and a sodium salt of the methyl ester of N-all-trans-retinoyl cysteic acid.

Example 2

Preparation of Amorphous Docetaxel 27 ml of a docetaxel stock solution in methanol (c=0.5 mg/ml) and 1 ml of an aqueous solution of a sodium salt of the methyl ester of N-all-trans-retinoyl cysteic acid (c=15 mg/ml) were combined in a 100 ml round bottom flask. The obtained solution was evaporated in vacuo to dryness; the residue was dissolved in 20 ml of methanol followed by a new evaporation of methanol in vacuo. The film obtained after the evaporation consisted of a mixture of amorphous docetaxel and a sodium salt of the methyl ester of N-13-cis-retinoyl cysteic acid.

Example 3

Dissolving of Amorphous Paclitaxel in Micellar Solution of a Sodium Salt of the Methyl Ester of N-all-Trans-Retinoyl Cysteic Acid 13 ml of water and 2 ml of an aqueous solution of a sodium salt of the methyl ester of N-all-trans-retinoyl cysteic acid (c=15 mg/ml) were added to the flask containing the film with amorphous paclitaxel prepared in Example 1. The paclitaxel film was completely dissolved by gentle shaking of the vial for 10 min. The obtained solution was clear and transparent. It contained dissolved paclitaxel in a concentration of 2 mg/ml. Filtration the solution through 0.2 µm filter did not result in any reduction of the paclitaxel concentration.

Example 4

Dissolving of Amorphous Docetaxel in Aqueous Solution of a Sodium Salt of the Methyl Ester of N-13-Cis-Retinoyl Cysteic Acid 24.4 ml of water was added to the amorphous docetaxel obtained in Example 2, and the mixture was stirred by magnetic stirrer for 5 minutes. Then 2.6 ml of an aqueous solution of a sodium salt of the methyl ester of N-13-cis-retinoyl cysteic acid (c=15 mg/ml) was added to the suspension and the mixture was stirred for 15 min. The obtained solution was clear and transparent. It contained dissolved docetaxel in a concentration of 0.5 mg/ml. Filtration the solution through 0.2 µm filter did not reveal any reduction of the docetaxel concentration.

Example 5

Preparation of Paclitaxel Aqueous Formulation by the Step-Wise Mixing of Aqueous Solution of a Mixture of a Sodium Salt of the Methyl Ester of N-all-Trans-Retinoyl Cysteic Acid and a Sodium Salt of the Methyl Ester of N-13-Cis-Retinoyl Cysteic Acid and Methanol Solution of Paclitaxel 10 ml of a methanol solution of paclitaxel (10 mg/ml) was added dropwise into a 500 ml round bottom flask containing 120 ml of an aqueous solution of a sodium salt of the methyl ester of N-all-trans-retinoyl cysteic acid (2.5 mg/ml) and a sodium salt of the methyl ester of N-13-cis-retinoyl cysteic acid (2.5 mg/ml) while stirring by means of a magnetic stirrer. Then the content of the flask was evaporated on a rotary evaporator at 90 rpm and a bath temperature 45° C. until the internal pressure of the closed vacuum system consisting of the flask, the evaporator and a vacuum pump dropped to 70 mbar. Such addition of paclitaxel methanol solution as described above followed by evaporation was repeated twice. The total volume of added methanol solution was 30 ml. The aqueous solution remaining after the evaporation was transferred from the flask into a 250 ml measuring cylinder. The flask was rinsed three times with 5 ml of water and the rinsing solutions were poured into the cylinder. To the combined solutions was added water to achieve a total volume 150 ml. The obtained solution was filtered through a 0.2 µm filter and freeze dried. The paclitaxel concentration in the obtained formulation was 2 mg/ml.

Example 6

Preparation of Docetaxel Aqueous Formulation by the Step-Wise Mixing of Aqueous Solution of a Sodium Salt of the Methyl Ester of N-all-Trans-Retinoyl Cysteic Acid and Ethanol Solution of Docetaxel 6 ml of a solution of docetaxel (5 mg/ml) in 95% ethanol was added dropwise into a 500 ml round bottom flask containing 100 ml of an aqueous solution of a sodium salt of the methyl ester of N-all-trans-retinoyl cysteic acid (3 mg/ml) while stirring by means of a magnetic stirrer. The main part of the ethanol was evaporated on a rotary evaporator at 90 rpm and a bath temperature 55° C. until the internal pressure of the closed vacuum system consisting of the flask, the evaporator and a vacuum pump dropped to 60 mbar. Such addition of docetaxel ethanol solution as described above followed by evaporation was repeated twice. The total volume of added ethanol solution was 30 ml. The aqueous solution remaining after the evaporation of ethanol was transferred from the flask into a 250 ml measuring cylinder. The flask was rinsed three times with 5 ml water and the rinsing solutions were poured into the cylinder. Water was added to the combined solutions to achieve a total volume 150 ml. After filtration through a 0.2 µm filter the formulation was freeze dried. The docetaxel concentration in the obtained formulation was 1 mg/ml.

Example 7

Preparation of Docetaxel Aqueous Formulation by the Mixing of Aqueous Solution of a Sodium Salt of the Methyl Ester of N-all-Trans-Retinoyl Cysteic Acid and a Sodium Salt of the Methyl Ester of N-13-Cis-Retinoyl Cysteic Acid and Ethanol Solution of Docetaxel During Evaporation A 1000 ml round bottom flask containing 150 ml of an aqueous solution of a sodium salt of the methyl ester of N-all-trans-retinoyl cysteic acid (3 mg/ml) and a sodium salt of the methyl ester of N-13-cis-retinoyl cysteic acid (3 mg/ml) was attached to a rotary evaporator equipped with an inlet pipe for feeding of alcohol solutions of taxanes in such a way that the inlet pipe did not come in touch with the aqueous solution. The evaporation started with a bath temperature of 45° C. and a rotation speed of 100 rpm. After 1 min dropwise addition (60 drops/min or 3 ml/min) of 80 ml of a methanol solution of docetaxel (5 mg/ml) was started. After this addition had been completed the evaporation was continued for 5 min. The aqueous solution remaining after the evaporation of methanol was transferred from the evaporating flask into a 250 ml measuring cylinder. The flask was rinsed three times with 10 ml water and the rinsing solutions were poured into the cylinder. Water was added to the combined solutions was added to achieve a total volume 200 ml. After filtration through a 0.2 μm filter the formulation was freeze dried. The docetaxel concentration in the obtained formulation was 2 mg/ml.

Example 8

Investigation of the Dependence of Particle Size on the w/w Ratio of a Sodium Salt of the Methyl Ester of N-all-Trans-Retinoyl Cysteic Acid/Paclitaxel in Formulations Formed by the Reconstitution of Freshly Evaporated Residues of a Sodium Salt of the Methyl Ester of N-all-Trans-Retinoyl Cysteic Acid and Paclitaxel with Aqueous Solution of Sodium Chloride in Concentration 9 mg/ml

TABLE 1

| w/w ratio of sodium salt of methyl ester of N-all-trans-retinoyl cysteic acid/paclitaxel | Paclitaxel concentration 0.5 mg/ml | | Paclitaxel concentration 1 mg/ml | | Paclitaxel concentration 2 mg/ml | | Paclitaxel concentration 4 mg/ml | |
|---|---|---|---|---|---|---|---|---|
| | Average particle size, nm | St. dev. | Average particle size, nm | St. dev. | Average particle size, nm | St. dev. | Average particle size, nm | St. dev. |
| 1.1 | 27.9 | 2.0 | 32.2 | 1.2 | 35.7 | 1.3 | 40.3 | 1.1 |
| 1.2 | 21.4 | 0.6 | 22.0 | 1.1 | 23.5 | 1.2 | 25.6 | 0.8 |
| 1.5 | 13.1 | 0.6 | 14.8 | 0.5 | 14.9 | 1.0 | 15.3 | 0.7 |
| 3.0 | 12.6 | 0.3 | 13.3 | 0.7 | 13.8 | 0.4 | 14.8 | 0.5 |
| 8.0 | 11.0 | 0.5 | 11.5 | 0.6 | 12.8 | 0.4 | 13.3 | 0.3 |

As shown in Table 1 and FIG. 1 the particle size decreases with the reduction of amount of paclitaxel which is loaded in micelles.

Example 9

Investigation of the Dependence of Particle Size of Docetaxel Formulation on the Concentration of Sodium Chloride The solutions were prepared by reconstitution of freeze-dried powder contained docetaxel and a sodium salt of the methyl ester of N-13-cis-retinoyl cysteic acid in the w/w ratio 1:1.

TABLE 2

| Concentration of NaCl, mg/ml | Docetaxel concentration 0.5 mg/ml | | Docetaxel concentration 1 mg/ml | | Docetaxel concentration 2 mg/ml | | Docetaxel concentration 4 mg/ml | |
|---|---|---|---|---|---|---|---|---|
| | Average size, nm | St. dev. | Average size, nm | St. dev. | Average size, nm | St. dev. | Average size, nm | St. dev. |
| 4 | 7.2 | 0.7 | 6.7 | 0.6 | 6.4 | 0.4 | 5.9 | 2.5 |
| 8 | 7.8 | 0.7 | 8.2 | 0.7 | 9.3 | 1.4 | 12.7 | 1.4 |
| 12 | 12.1 | 1.0 | 13.4 | 0.9 | 14.6 | 1.0 | 40.0 | 4.9 |
| 16 | 17.0 | 2.3 | 29.0 | 4.2 | 51.3 | 3.7 | 82.7 | 3.7 |
| 20 | 22.4 | 1.8 | 39.3 | 2.8 | 72.3 | 3.7 | 107.7 | 6.2 |
| 24 | 28.3 | 4.6 | 86.0 | 4.2 | 108.3 | 7.5 | 144.3 | 9.9 |

Figure 2:
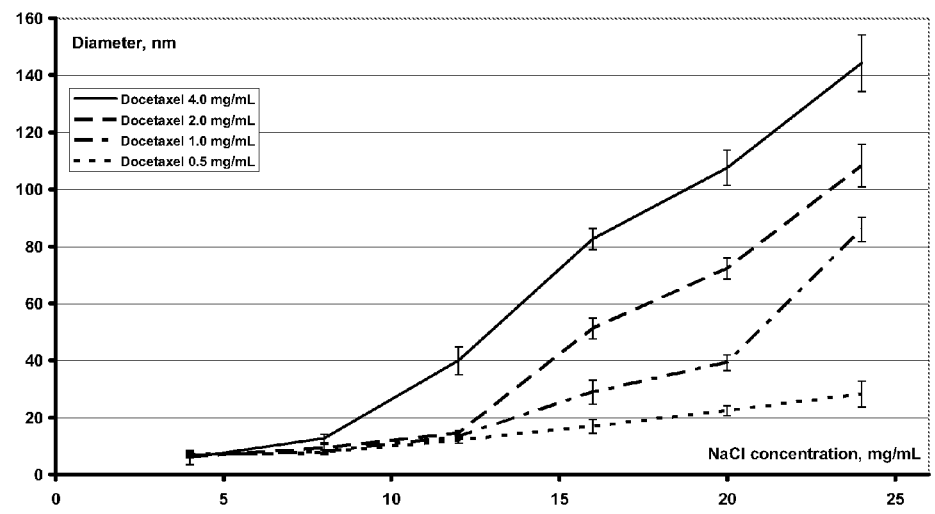
FIG. 2 shows the dependence of the size of particles formed by sodium salt of methyl ester of N-13-cis-retinoyl cysteic acid and docetaxel (w/w ratio 1:1) on the concentration of sodium chloride at different docetaxel concentrations.

As shown in Table 2 and FIG. 2 the increase in concentration of sodium chloride, i.e. ionic strength, makes the particles larger.

Example 10

Transformation of a Sodium Salt of the Methyl Ester of N-all-Trans-Retinoyl Cysteic Acid into its Calcium Salt Aqueous solutions of a sodium salt of the methyl ester of N-all-trans-retinoyl cysteic acid (5 ml, 15 mg/ml) and calcium chloride (3 ml, 30 mg/ml) were mixed in a 10 ml test tube. During the mixing a fine precipitation emerged. The precipitate was separated by centrifugation of the test tube at 3000 rpm for 10 min. The supernatant was removed and the precipitate was shaken with 8 ml of water followed by a new centrifugation. After three additional washing procedures as described above the supernatant was filtered through a 0.2 μm filter in order to remove possible large aggregates of the product. The solubility of the calcium salt of the methyl ester of N-all-trans-retinoyl cysteic acid corresponded to its concentration in the filtered solution and was equal to 0.2 mg/ml as measured by the UV method described above. The reaction is illustrated by the below general scheme involving chlorides of any polyvalent metal ions, not only calcium ions.

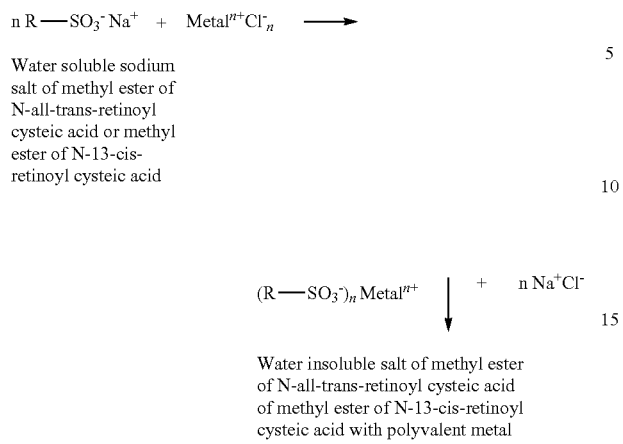

Example 11

Investigation of the Dependence of Particle Size of Paclitaxel Formulation on the Concentration of Calcium Chloride Solutions were prepared by reconstitution of freeze-dried powder containing paclitaxel, a sodium salt of the methyl ester of N-all-trans-retinoyl cysteic acid and a sodium salt of the methyl ester of N-13-cis-retinoyl cysteic acid in the w/w/w ratio 1:1:1. Solvents for the reconstitution were prepared by dissolving of appropriate amounts of calcium chloride dihydrate in an aqueous solution of sodium chloride with a concentration 9 mg/ml.

TABLE 3

| Concentration of $CaCl_2$, mmol/l | Paclitaxel concentration 0.5 mg/ml | | Paclitaxel concentration 1 mg/ml | | Paclitaxel concentration 2 mg/ml | |
|---|---|---|---|---|---|---|
| | Average particle size, nm | St. dev. | Average particle size, nm | St. dev. | Average particle size, nm | St. dev. |
| 0 | 12.7 | 0.4 | 16.3 | 1.1 | 22.1 | 0.2 |
| 2 | 23.8 | 1.7 | 24.6 | 0.5 | 27.3 | 0.2 |
| 4 | 27.4 | 0.2 | 30.1 | 0.4 | 32.0 | 0.1 |
| 6 | 51.0 | 0.6 | 55.2 | 5.1 | 58.6 | 1.6 |

Figure 3:
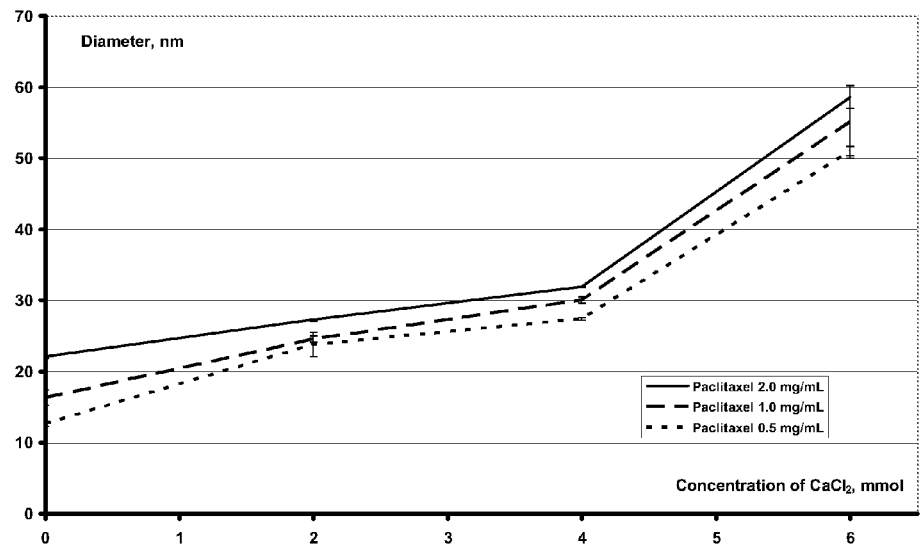
FIG. 3 shows the dependence of the size of particles formed by sodium salt of methyl ester of N-all-trans-retinoyl cysteic acid and paclitaxel (w/w ratio of paclitaxel:methyl ester of N-all-trans-retinoyl cysteic acid is 1:2) on the concentration of calcium chloride in an aqueous solution of sodium chloride at a concentration of 9 mg/ml.

As shown in Table 3 and FIG. 3 the size of particles in the formulations increases almost linearly with the increase of $CaCl_2$ concentration.

Example 12

Time Course of Particle Size and Zeta-Potential of Formulation Obtained by Reconstitution of Freeze Dried Mixture of Paclitaxel, a Sodium Salt of the Methyl Ester of N-all-Trans-Retinoyl Cysteic Acid and a Sodium Salt of the Methyl Ester of N-13-Cis-Retinoyl Cysteic Acid in w/w/w Ratio 1:0.75:0.75 in Aqueous Solution of Sodium Chloride (9 mg/ml), Calcium Chloride (2 mmol/l) and Magnesium Chloride (1 mmol/l)

TABLE 4

| Time after reconstitution | Paclitaxel concentration 0.5 mg/ml | | Paclitaxel concentration 1 mg/ml | | Paclitaxel concentration 2 mg/ml | |
|---|---|---|---|---|---|---|
| | Average particle size, nm | St. dev. | Average particle size, nm | St. dev. | Average particle size, nm | St. dev. |
| 0 | 22.1 | 0.5 | 23.5 | 0.5 | 25.6 | 0.8 |
| 1 | 22.7 | 0.7 | 24.1 | 0.8 | 26.3 | 0.7 |
| 2 | 23.1 | 0.5 | 24.3 | 0.4 | 26.2 | 0.5 |
| 4 | 23 | 0.4 | 24.4 | 0.3 | 26.6 | 0.2 |
| 8 | 23.4 | 0.7 | 24.0 | 0.6 | 27.0 | 0.4 |

TABLE 5

| Time after reconstitution | Paclitaxel concentration 0.5 mg/ml | | Paclitaxel concentration 1 mg/ml | | Paclitaxel concentration 2 mg/ml | |
|---|---|---|---|---|---|---|
| | Zeta-potential, mV | St. dev. | Zeta-potential, mV | St. dev. | Zeta-potential, mV | St. dev. |
| 0 | −24.5 | 1.3 | −28.7 | 1.2 | −29.9 | 1.1 |
| 1 | −26.3 | 1.8 | −30.1 | 1.0 | −32.7 | 0.8 |
| 2 | −25.2 | 0.4 | −30.4 | 1.0 | −30.6 | 0.5 |
| 4 | −27.0 | 0.5 | −29.6 | 0.6 | −31.2 | 0.3 |
| 8 | −27.1 | 0.4 | −30.4 | 0.3 | −32.4 | 0.6 |

Figure 4:
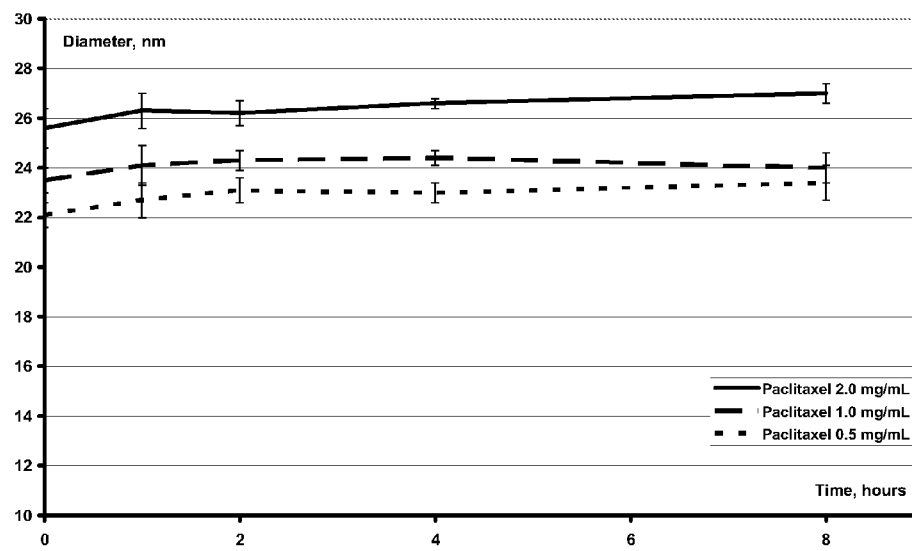
FIGS. 4 and 5 show the time course of particle size and Z-potential of a formulation obtained by reconstitution of a freeze dried mixture of paclitaxel, sodium salt of methyl ester of N-all-trans-retinoyl cysteic acid and sodium salt of methyl ester of N-13-cis-retinoyl cysteic acid in w/w/w ratio 1:0.75:0.75 in an aqueous solution of sodium chloride (9 mg/ml), calcium chloride (2 mmol/l) and magnesium chloride (1 mmol/l).
Figure 5:
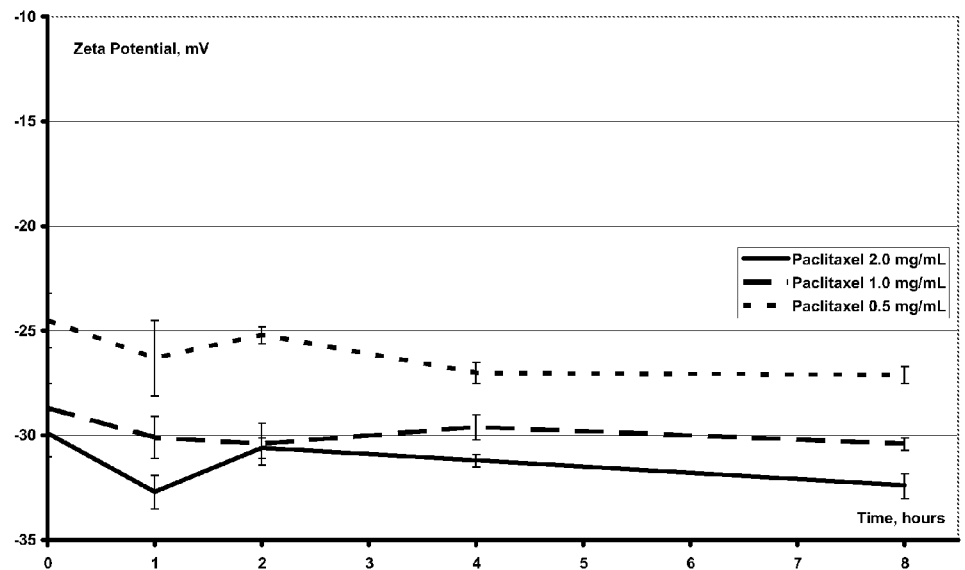

Table 4 and 5, and FIGS. 4 and 5 show that there are no any significant changes in the values of the particle size as well as Zeta-potential during storage of the formulation for 8 hours.

Example 13

Time Course of Particle Size and Zeta-Potential of Formulation Obtained by Reconstitution of Freeze Dried Mixture of Docetaxel and a Sodium Salt of the Methyl Ester of N-all-Trans-Retinoyl Cysteic Acid in w/w Ratio 1:2 in Aqueous Solution of Sodium Chloride (9 mg/ml) and Calcium Chloride (3 mmol/l)

TABLE 6

| Time after re-constitution | Docetaxel concentration 0.5 mg/ml | | Docetaxel concentration 1 mg/ml | | Docetaxel concentration 2 mg/ml | |
|---|---|---|---|---|---|---|
| | Average particle size, nm | St. dev. | Average particle size, nm | St. dev. | Average particle size, nm | St. dev. |
| 0 | 11.9 | 0.3 | 12.6 | 0.2 | 13.1 | 0.4 |
| 1 | 12.3 | 0.3 | 13.2 | 0.4 | 13.4 | 0.2 |
| 2 | 12.4 | 0.2 | 13.0 | 0.2 | 13.7 | 0.4 |
| 4 | 12.2 | 0.4 | 12.9 | 0.1 | 13.4 | 0.2 |
| 8 | 12.5 | 0.3 | 13.2 | 0.2 | 13.8 | 0.2 |

TABLE 7

| Time after reconstitution | Paclitaxel concentration 0.5 mg/ml | | Paclitaxel concentration 1 mg/ml | | Paclitaxel concentration 2 mg/ml | |
|---|---|---|---|---|---|---|
| | Zeta-potential, mV | St. dev. | Zeta-potential, mV | St. dev. | Zeta-potential, mV | St. dev. |
| 0 | −22.2 | 2.1 | −22.6 | 1.3 | −22.8 | 0.6 |
| 1 | −23.4 | 0.9 | −22.4 | 1.2 | −24.1 | 0.8 |
| 2 | −22.7 | 0.4 | −23.7 | 0.9 | −23.3 | 0.4 |
| 4 | −21.9 | 0.3 | −23.1 | 0.8 | −23.1 | 0.2 |
| 8 | −21.7 | 0.6 | −23.4 | 0.6 | −23.5 | 0.5 |

Figure 6:
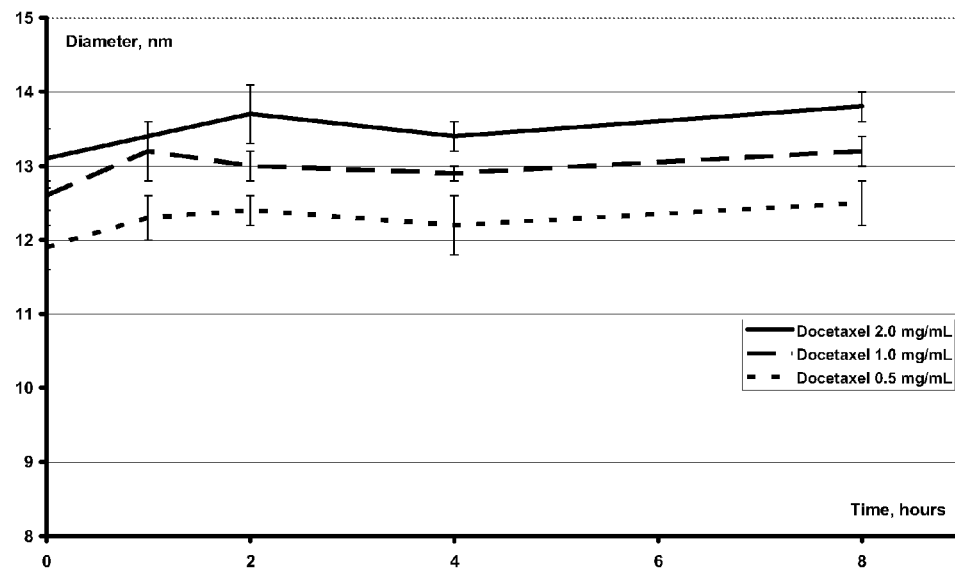
FIGS. 6 and 7 show the time course of particle size and Z-potential of a formulation obtained by reconstitution of a freeze dried mixture of docetaxel and sodium salt of methyl ester of N-all-trans-retinoyl cysteic acid in w/w ratio 1:2 in an aqueous solution of sodium chloride (9 mg/ml) and calcium chloride (3 mmol/l)
Figure 7:
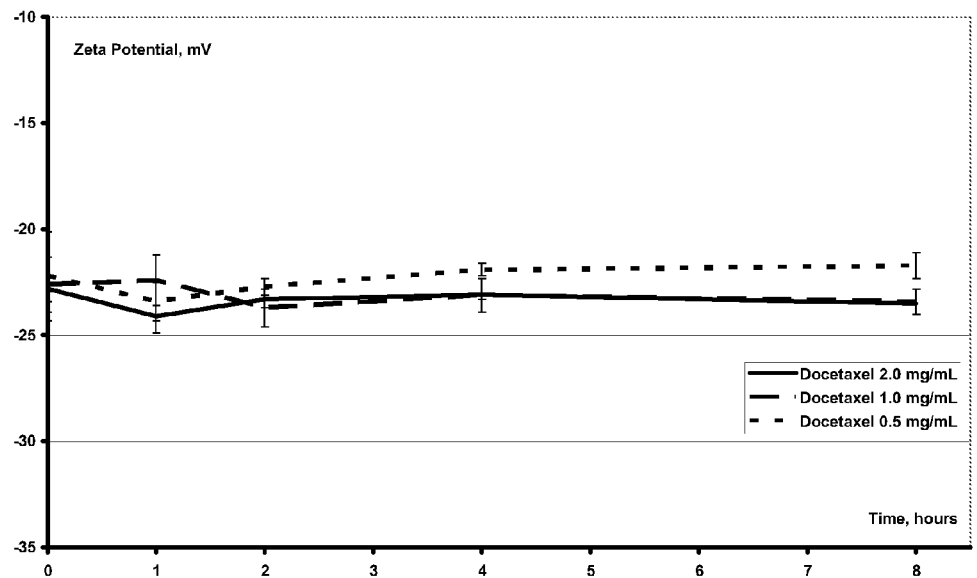

Table 6 and 7, and FIGS. 6 and 7 show that there are no any significant changes in the values of the particle size as well as Zeta-potential during storage of the formulation for 8 hours.

Example 14

Preparation of Amorphous Ciclosporin A 50 ml of a Ciclosporin A stock solution in methanol (c=1.0 mg/ml) and 4.2 ml of an aqueous solution of a sodium salt of the methyl ester of N-all-trans-retinoyl cysteic acid (c=12 mg/ml) were evaporated in vacuo to dryness in a 100 ml round bottom flask. 15 ml of methanol was added to the flask and the residue was dissolved. The obtained solution was evaporated to dryness. The film obtained after the evaporation consisted of a mixture of amorphous Ciclosporin A and a sodium salt of the methyl ester of N-all-trans-retinoyl cysteic acid.

Example 15

Dissolving of Amorphous Ciclosporin a in Micellar Solution of a Sodium Salt of the Methyl Ester of N-all-Trans-Retinoyl Cysteic Acid 45.8 ml of water and 4.2 ml of an aqueous solution of a sodium salt of the methyl ester of N-all-trans-retinoyl cysteic acid (c=12 mg/ml) were added to the flask containing the film with amorphous Ciclosporin A prepared in Example No 14. The Ciclosporin A film was completely dissolved by gentle shaking of the vial for 10 min. The obtained solution was clear and transparent. It contained dissolved Ciclosporin A in a concentration of 1 mg/ml. Filtration the solution through 0.2 μm filter did not result in any reduction of the Ciclosporin A concentration.

Example 16

Investigation of the Dependence of Particle Size on the w/w Ratio of a Sodium Salt of the Methyl Ester of N-all-Trans-Retinoyl Cysteic Acid/Ciclosporin a in Formulations Formed by the Reconstitution of Freshly Evaporated Residues of a Sodium Salt of the Methyl Ester of N-all-Trans-Retinoyl Cysteic Acid and Ciclosporin a with Aqueous Solution of Sodium Chloride in Concentration 9 mg/ml

TABLE 8

| w/w ratio of sodium salt of methyl ester of N-all-trans-retinoyl cysteic acid/Ciclosporin A | Ciclosporin A concentration 0.5 mg/ml | | Ciclosporin A concentration 1 mg/ml | | Ciclosporin A concentration 2 mg/ml | | Ciclosporin A concentration 4 mg/ml | |
|---|---|---|---|---|---|---|---|---|
| | Average particle size, nm | St. dev. | Average particle size, nm | St. dev. | Average particle size, nm | St. dev. | Average particle size, nm | St. dev. |
| 1.3 | 57.3 | 1.6 | 63.2 | 2.2 | 69.7 | 2.0 | 78.0 | 3.6 |
| 1.4 | 42.2 | 1.8 | 46.9 | 1.8 | 50.8 | 1.8 | 58.8 | 2.7 |
| 1.6 | 28.6 | 1.4 | 30.9 | 1.7 | 32.3 | 1.1 | 37.8 | 2.5 |
| 2.0 | 20.2 | 1.2 | 22.1 | 1.1 | 25.5 | 0.6 | 25.9 | 0.9 |
| 8.0 | 10.4 | 0.8 | 11.5 | 0.4 | 11.9 | 0.5 | 12.9 | 0.5 |

Figure 10:
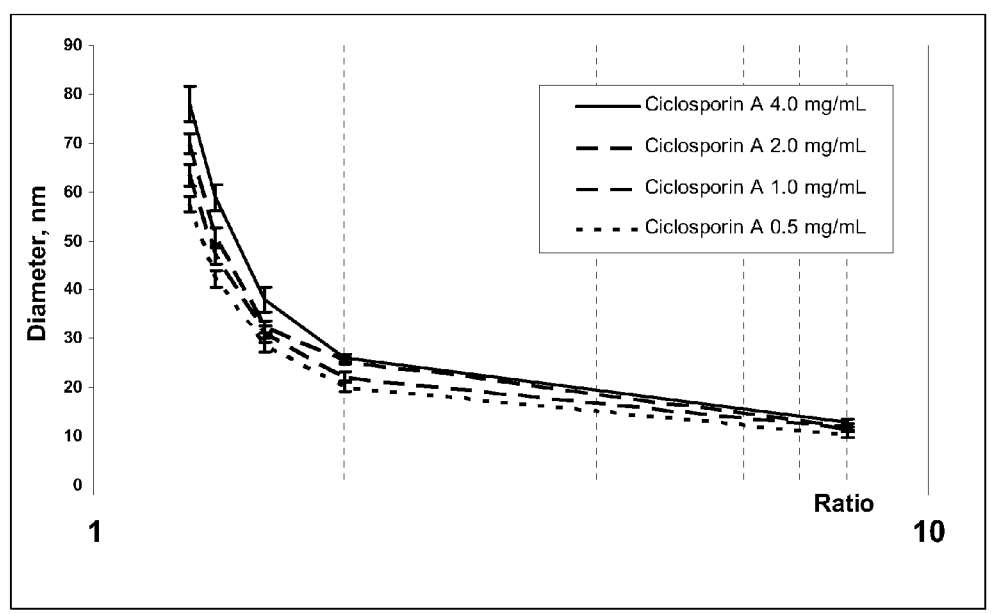
FIG. 10 shows the dependence of the particle size on the w/w ratio of sodium salt of methyl ester of N-all-trans-retinoyl cysteic acid to Ciclosporin A at different Ciclosporin A concentrations in an aqueous solution of sodium chloride at a concentration of 9 mg/ml.

As shown in Table 8 and FIG. 10 the particle size decreases with the reduction of amount of Ciclosporin A which is loaded in micelles.

Biological Evaluation

Examples 17-21

In vitro experiments showed that the activity of taxane formulations in different solid tumour cell lines is more expressed by the use of nanoparticles as provided by the present invention. Moreover the cytotoxicity of these formulations dramatically depends on the size of the nanoparticles. Bigger size of the nanoparticles in the inventive drug delivery system leads to diminished transport of taxanes in a cell, which in turn results in reduction of the cytotoxicity.

The highest activity was observed when the size was 25 and 13 nm for paclitaxel and docetaxel solutions, respectively: in vitro experiments gave enhancement factors for these formulations of 41.7 and 31.7, respectively, on day 3 of exposure. The control sample in this experiment contained taxanes in ethanol solutions (without any nanoparticles).

Other in vitro comparisons of taxane formulations according to the invention with commercially available taxane formulations showed that the formulations according to the invention possess more expressed cytotoxic activity against different malignant cell culture lines like breast adenocarcinoma, ovary adenocarcinoma and lung non-small cell cancer.

Example 17

Comparative Evaluation of the Cytotoxicity of the Formulations Formed by Docetaxel-Sodium Salt of the Methyl Ester of N-all-Trans-Retinoyl Cysteic Acid-Sodium Salt of the Methyl Ester of N-13-Cis-Retinoyl Cysteic Acid Mixture (w/w/w=1:1:1) in Cultures of Human Ovary Adenocarcinoma SKOV3 Cell Line Freeze dried powder consisted of docetaxel, a sodium salt of the methyl ester of N-all-trans-retinoyl cysteic acid and a sodium salt of the methyl ester of N-13-cis-retinoyl cysteic acid was dissolved in either 70% ethanol or sodium chloride solution (9 mg/ml) containing an appropriate amount of calcium chloride. Samples of the solutions obtained were taken and used for measurement of average particle size.

TABLE 9

| Solvent | Concentration of $CaCl_2$, mmol/l | Particle size, nm | Day 3 $IC_{50}$ | EF* day 3 | Day 4 $IC_{50}$ | EF* day 4 | Day 5 $IC_{50}$ | EF* day 5 |
|---|---|---|---|---|---|---|---|---|
| 70% EtOH | — | — | $2.0 \cdot 10^{-7}$ | — | $7.2 \cdot 10^{-9}$ | — | $7.6 \cdot 10^{-10}$ | — |
| NaCl solution | 0 | 11.3 | $1.2 \cdot 10^{-7}$ | 1.7 | $7.2 \cdot 10^{-9}$ | 1 | $6.5 \cdot 10^{-10}$ | 1.2 |
| NaCl solution | 1 | 12.2 | $3.4 \cdot 10^{-8}$ | 5.9 | $5.6 \cdot 10^{-9}$ | 1.3 | $4.2 \cdot 10^{-10}$ | 1.8 |
| NaCl solution | 2 | 13.1 | $6.3 \cdot 10^{-9}$ | 31.7 | $2.1 \cdot 10^{-9}$ | 3.4 | $9.4 \cdot 10^{-11}$ | 8.1 |
| NaCl solution | 3 | 14.6 | $2.0 \cdot 10^{-8}$ | 10 | $3.4 \cdot 10^{-9}$ | 2.1 | $1.4 \cdot 10^{-10}$ | 5.4 |

Figure 8:
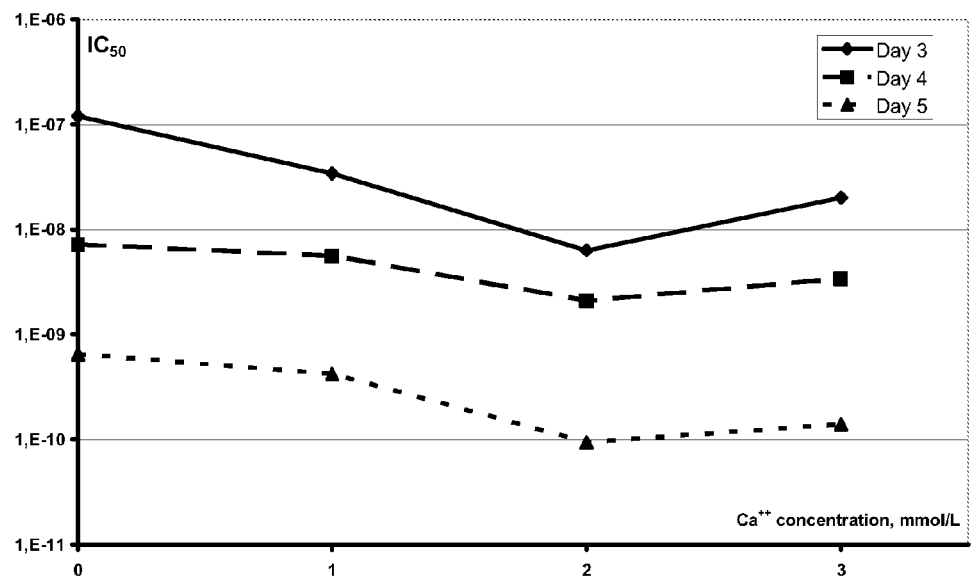
FIG. 8 shows a comparative evaluation of the cytotoxicity of the formulations formed by docetaxel-sodium salt of methyl ester of N-all-trans-retinoyl cysteic acid-sodium salt of methyl ester of N-13-cis-retinoyl cysteic acid mixture (w/w/w=1:1:1) in cultures of human ovary adenocarcinoma SKOV3 cell line.

*The formulation with ethanol was used as positive control for calculation of EF Table 9 and FIG. 8 show that the formulation contained 2 mmol/l of calcium is the most active. Then with increase and decrease of calcium concentration the cytotoxicity of the formulations is reduced.

Example 18

Comparative Evaluation of the Cytotoxicity of the Formulations Formed by Paclitaxel-Sodium Salt of the Methyl Ester of N-all-Trans-Retinoyl Cysteic Acid-Sodium Salt of the Methyl Ester N-13-Cis-Retinoyl Cysteic Acid Mixture (w/w/w=1:0.75:0.75) in Cultures of Human Ovary Adenocarcinoma SKOV3 Cell Line Freeze dried powder consisting of paclitaxel, a sodium salt of the methyl ester of N-all-trans-retinoyl cysteic acid and a sodium salt of the methyl ester of N-13-cis-retinoyl cysteic acid was dissolved in either 70% ethanol or sodium chloride solution (9 mg/ml) containing an appropriate amount of calcium chloride. Samples of the solutions obtained were taken and used for measurement of average particle size.

TABLE 10

| Solvent | Concentration of $CaCl_2$, mmol/l | Particle size, nm | Day 3 $IC_{50}$ | EF* day3 | Day 4 $IC_{50}$ | EF* day4 | Day 5 $IC_{50}$ | EF* day5 |
|---|---|---|---|---|---|---|---|---|
| 70% EtOH | — | — | $5.0 \cdot 10^{-6}$ | — | $2.1 \cdot 10^{-7}$ | — | $6.8 \cdot 10^{-8}$ | — |
| NaCl solution | 0 | 17 | $3.0 \cdot 10^{-6}$ | 1.7 | $1.3 \cdot 10^{-7}$ | 1.6 | $5.5 \cdot 10^{-8}$ | 1.2 |
| NaCl solution | 1 | 19 | $1.7 \cdot 10^{-6}$ | 2.9 | $8.4 \cdot 10^{-8}$ | 2.5 | $9.8 \cdot 10^{-9}$ | 6.9 |
| NaCl solution | 2 | 25 | $1.2 \cdot 10^{-7}$ | 41.7 | $2.3 \cdot 10^{-8}$ | 9.1 | $7.2 \cdot 10^{-10}$ | 94.0 |
| NaCl solution | 3 | 29 | $2.4 \cdot 10^{-7}$ | 20.8 | $4.3 \cdot 10^{-8}$ | 4.9 | $1.2 \cdot 10^{-8}$ | 5.7 |

Figure 9:
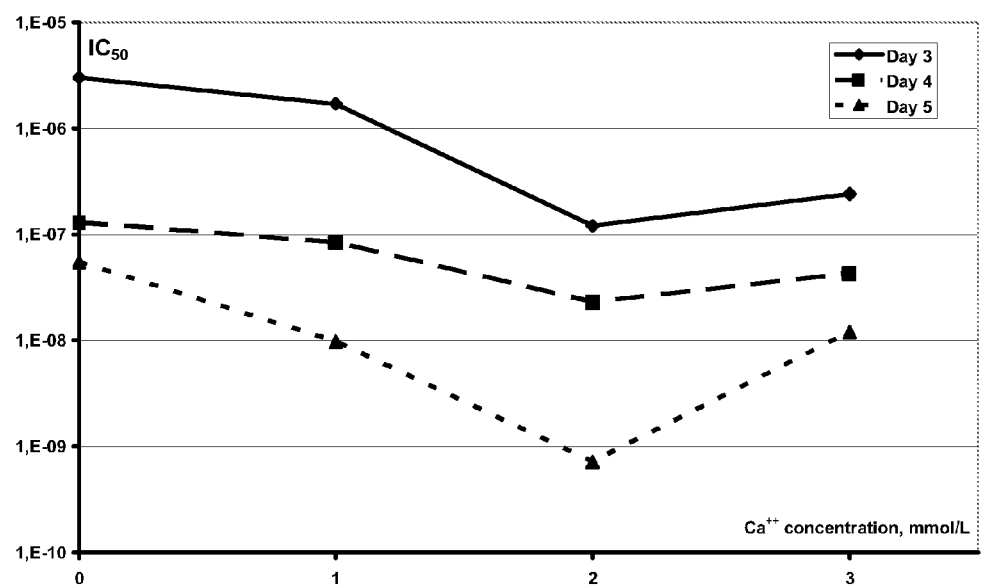
FIG. 9 shows a comparative evaluation of the cytotoxicity of the formulations formed by paclitaxel-sodium salt of methyl ester of N-all-trans-retinoyl cysteic acid-sodium salt of methyl ester of N-13-cis-retinoyl cysteic acid mixture (w/w/w=1:0.75:0.75) in cultures of human ovary adenocarcinoma SKOV3 Cell Line.

*The formulation with ethanol was used as positive control for calculation of EF Table 10 and FIG. 9 show that the formulation contained 2 mmol/l of calcium is the most active. Then with increase and decrease of calcium concentration the cytotoxicity of the formulations is reduced.

Example 19

Evaluation of Cytotoxicity of the Formulation "Paclitaxel-Sodium Salt of the Methyl Ester of N-all-Trans-Retinoyl Cysteic Acid-Sodium Salt of the Methyl Ester of N-13-Cis-Retinoyl Cysteic Acid (w/w/w 1:0.75:075)" with TAXOL®, ABRAX-ANE® and Paclitaxel Alone in Cultures of Human Breast Adenocarcinoma MDA-MB-231 Cell Line The title formulation was prepared by dissolving freeze dried powder in an aqueous solution containing sodium chloride (6 mg/ml), potassium chloride (0.3 mg/ml), calcium chloride hexahydrate (0.4 mg/ml), sodium lactate (3.1 mg/ml). Paclitaxel was used in a methanol solution. TAXOL® and ABRAXANE® samples were prepared according to instructions from the manufacturers by dilution of a commercially available TAXOL® concentrate (6 mg/ml) in sodium chloride (9 mg/ml) solution and by reconstitution of freeze dried albumin-bound paclitaxel with sodium chloride (9 mg/ml) solution to a paclitaxel concentration of 5 mg/ml. All samples were used within one hour after preparation. Enhancement effects were calculated versus paclitaxel methanol solution. The results are set forth in Table 11 below.

TABLE 11

| Formulation | Particle size, nm | $IC_{50}$ day 3 | EF day 3 | $IC_{50}$ day4 | EF day 4 |
|---|---|---|---|---|---|
| Paclitaxel | — | $(3.80 \pm 0.15) \times 10^{-8}$ | — | $(3.4 \pm 0.12) \times 10^{-8}$ | — |
| TAXOL ® | — | $(2.04 \pm 0.05) \times 10^{-8}$ | 1.9 | $(2.0 \pm 0.10) \times 10^{-8}$ | 1.7 |
| ABRAXANE ® | 130 | $(4.2 \pm 0.09) \times 10^{-8}$ | 0.9 | $(3.4 \pm 0.16) \times 10^{-8}$ | 1 |
| Paclitaxel-sodium salt of methyl ester of N-all-trans-retinoyl cysteic acid-sodium salt of methyl ester of N-13-cis-retinoyl cysteic acid | 24 | $(4.2 \pm 0.14) \times 10^{-9}$ | 4.9 | $(3.2 \pm 0.09) \times 10^{-9}$ | 10.6 |

Example 20

Evaluation of Cytotoxicity of the Formulation "Docetaxel-Sodium Salt of the Methyl Ester of N-all-Trans-Retinoyl Cysteic Acid-Sodium Salt of the Methyl Ester of N-13-Cis-Retinoyl Cysteic Acid (w/w/w 1:0.5:0.5)" with TAXOTERE® and Docetaxel Alone in Cultures of Human Breast Adenocarcinoma MDA-MB-231 Cell Line The title formulation was prepared by dissolving freeze dried powder in an aqueous solution containing sodium chloride (6 mg/ml), potassium chloride (0.3 mg/ml), calcium chloride hexahydrate (0.4 mg/ml), sodium lactate (3.1 mg/ml). Docetaxel was used in a methanol solution. TAXOTERE® sample was prepared according to instructions from the manufacturer by dilution of a commercially available concentrate (40 mg/ml) firstly with ethanol solution to concentration 10 mg/ml followed by further dilution in sodium chloride (9 mg/ml) solution. All samples were used within one hour after preparation. Enhancement effects were calculated versus docetaxel methanol solution. The results are set forth in Table 12 below.

TABLE 12

| Formulation | Particle size, nm | $IC_{50}$ day 3 | EF day 3 | $IC_{50}$ day4 | EF day 4 |
|---|---|---|---|---|---|
| Docetaxel | — | $(1.25 \pm 0.11) \times 10^{-8}$ | — | $(1.0 \pm 0.1) \times 10^{-8}$ | — |
| TAXOTERE ® | — | $(1.08 \pm 0.09) \times 10^{-8}$ | 1.2 | $(9.60 \pm 0.18) \times 10^{-9}$ | 1.0 |
| Docetaxel-sodium salt of methyl ester of N-all-trans-retinoyl cysteic acid-sodium salt of methyl ester of N-13-cis-retinoyl cysteic acid | 12 | $(3.1 \pm 0.1) \times 10^{-9}$ | 4.0 | $(1.2 \pm 0.1) \times 10^{-9}$ | 8.3 |

Example 21

Evaluation of Cytotoxicity of the Formulation "Paclitaxel-Sodium Salt of the Methyl Ester of N-all-Trans-Retinoyl Cysteic Acid-Sodium Salt of the Methyl Ester of N-13-Cis-Retinoyl Cysteic Acid (w/w/w 1:0.75:075)" with TAXOL®, ABRAXANE® and Paclitaxel Alone in Cultures of Human Ovary Adenocarcinoma SKOV-3 Cell Line The title formulation was prepared by dissolving freeze dried powder in an aqueous solution containing sodium chloride (6 mg/ml), potassium chloride (0.3 mg/ml), calcium chloride hexahydrate (0.4 mg/ml), sodium lactate (3.1 mg/ml). Paclitaxel was used in a methanol solution. TAXOL® and ABRAXANE® samples were prepared according to instructions from the manufacturers by dilution of a commercially available TAXOL® concentrate (6 mg/ml) in sodium chloride (9 mg/ml) solution and by reconstitution of freeze dried albumin-bound paclitaxel with sodium chloride (9 mg/ml) solution to a paclitaxel concentration of 5 mg/ml. All samples were used within one hour after preparation. Enhancement effects were calculated versus paclitaxel methanol solution. The results are set forth in Table 13 below.

TABLE 13

| Formulation | Particle size, nm | $IC_{50}$ day 3 | EF day 3 | $IC_{50}$ day4 | EF day 4 |
|---|---|---|---|---|---|
| Paclitaxel | — | $(5.94 \pm 0.21) \times 10^{-7}$ | — | $(6.22 \pm 0.18) \times 10^{-8}$ | — |
| TAXOL ® | — | $(3.24 \pm 0.16) \times 10^{-7}$ | 1.8 | $(4.20 \pm 0.25) \times 10^{-8}$ | 1.5 |
| ABRAXANE ® | 130 | $(6.3 \pm 0.32) \times 10^{-7}$ | 0.94 | $(6.5 \pm 0.30) \times 10^{-8}$ | 0.96 |
| Paclitaxel-sodium salt of methyl ester of N-all-trans-retinoyl cysteic acid-sodium salt of methyl ester of N-13-cis-retinoyl cysteic acid | 24 | $(2.05 \pm 0.08) \times 10^{-7}$ | 2.3 | $(2.17 \pm 0.15) \times 10^{-8}$ | 2.9 |

Example 22

Evaluation of Cytotoxicity of the Formulation "Docetaxel-Sodium Salt of the Methyl Ester of N-all-Trans-Retinoyl Cysteic Acid-Sodium Salt of the Methyl Ester of N-13-Cis-Retinoyl Cysteic Acid (w/w/w 1:0.5:0.5)" with TAXOTERE® and Docetaxel Alone in Cultures of Human Ovary Adenocarcinoma SKOV-3 Cell Line The title formulation was prepared by dissolving freeze dried powder in an aqueous solution containing sodium chloride (6 mg/ml), potassium chloride (0.3 mg/ml), calcium chloride hexahydrate (0.4 mg/ml), sodium lactate (3.1 mg/ml). Docetaxel was used in a methanol solution. TAXOTERE® sample was prepared according to instructions from the manufacturer by dilution of a commercially available concentrate (40 mg/ml) firstly with ethanol solution to concentration 10 mg/ml followed by further dilution in sodium chloride (9 mg/ml) solution. All samples were used within one hour after preparation. Enhancement effects were calculated versus docetaxel methanol solution. The results are set forth in Table 14 below.

TABLE 14

| Formulation | Particle size, nm | $IC_{50}$ day 3 | EF day 3 | $IC_{50}$ day4 | EF day 4 |
|---|---|---|---|---|---|
| Docetaxel | — | $(9.07 \pm 0.38) \times 10^{-8}$ | — | $(2.85 \pm 0.26) \times 10^{-8}$ | — |
| TAXOTERE ® | — | $(1.18 \pm 0.09) \times 10^{-7}$ | 0.8 | $(2.03 \pm 0.15) \times 10^{-8}$ | 1.4 |
| Docetaxel-sodium salt of methyl ester of N-all-trans-retinoyl cysteic acid-sodium salt of methyl ester of N-13-cis-retinoyl cysteic acid | 12 | $(3.24 \pm 0.18) \times 10^{-8}$ | 2.8 | $(2.86 \pm 0.13) \times 10^{-9}$ | 10.0 |

Example 23

Evaluation of Cytotoxicity of the Formulation "Paclitaxel-Sodium Salt of the Methyl Ester of N-all-Trans-Retinoyl Cysteic Acid-Sodium Salt of the Methyl Ester of N-13-Cis-Retinoyl Cysteic Acid (w/w/w 1:0.75:075)" with TAXOL®, ABRAXANE® and Paclitaxel Alone in Cultures of Human Lung Non-Small Cancer Cell Line A549

The title formulation was prepared by dissolving freeze dried powder in an aqueous solution containing sodium chloride (6 mg/ml), potassium chloride (0.3 mg/ml), calcium chloride hexahydrate (0.4 mg/ml), sodium lactate (3.1 mg/ml). Paclitaxel was used in a methanol solution. TAXOL® and ABRAXANE® samples were prepared according to instructions from the manufacturers by dilution of a commercially available TAXOL® concentrate (6 mg/ml) in sodium chloride (9 mg/ml) solution and by a reconstitution of freeze dried albumin-bound paclitaxel with sodium chloride (9 mg/ml) solution to a paclitaxel concentration of 5 mg/ml. All samples were used within one hour after preparation. Enhancement effects were calculated versus paclitaxel methanol solution. The results are set forth in Table 15 below.

TABLE 15

| Formulation | Particle size, nm | $IC_{50}$ day 3 | EF day 3 | $IC_{50}$ day4 | EF day 4 |
|---|---|---|---|---|---|
| Paclitaxel | — | $(8.02 \pm 0.11) \times 10^{-9}$ | — | $(5.28 \pm 0.13) \times 10^{-9}$ | — |
| TAXOL ® | — | $(6.49 \pm 0.08) \times 10^{-9}$ | 1.2 | $(3.77 \pm 0.09) \times 10^{-9}$ | 1.4 |
| ABRAXANE ® | 130 | $(1.2 \pm 0.06) \times 10^{-8}$ | 0.67 | $(5.2 \pm 0.15) \times 10^{-9}$ | 1 |
| Paclitaxel-sodium salt of methyl ester of N-all-trans-retinoyl cysteic acid-sodium salt of methyl ester of N-13-cis-retinoyl cysteic acid | 24 | $(1.61 \pm 0.11) \times 10^{-9}$ | 5.0 | $(7.02 \pm 0.12) \times 10^{-10}$ | 7.5 |

Example 24

Evaluation of Cytotoxicity of the Formulation "Docetaxel-Sodium Salt of the Methyl Ester of N-all-Trans-Retinoyl Cysteic Acid-Sodium Salt of the Methyl Ester of N-13-Cis-Retinoyl Cysteic Acid (w/w/w 1:0.5:0.5)" with TAXOTERE® and Docetaxel Alone in Cultures of Human Lung Non-Small Cancer Cell Line A549

The title formulation was prepared by dissolving freeze dried powder in an aqueous solution containing sodium chloride (6 mg/ml), potassium chloride (0.3 mg/ml), calcium chloride hexahydrate (0.4 mg/ml), sodium lactate (3.1 mg/ml). Docetaxel was used in a methanol solution. TAXOTERE® sample was prepared according to instructions from the manufacturer by dilution of a commercially available concentrate (40 mg/ml) firstly with ethanol solution to concentration 10 mg/ml followed by further dilution in sodium chloride (9 mg/ml) solution. All samples were used within one hour after preparation. Enhancement effects were calculated versus docetaxel methanol solution. The results are set forth in Table 16 below.

TABLE 16

| Formulation | Particle size, nm | $IC_{50}$ day 3 | EF day 3 | $IC_{50}$ day4 | EF day 4 |
|---|---|---|---|---|---|
| Docetaxel | — | $(5.76 \pm 0.26) \times 10^{-9}$ | — | $(4.97 \pm 0.27) \times 10^{-9}$ | — |
| TAXOTERE ® | — | $(4.81 \pm 0.34) \times 10^{-9}$ | 1.2 | $(4.63 \pm 0.17) \times 10^{-9}$ | 1.1 |
| Docetaxel-sodium salt of methyl ester of N-all-trans-retinoyl cysteic acid-sodium salt of methyl ester of N-13-cis-retinoyl cysteic acid | 12 | $(9.14 \pm 0.47) \times 10^{-10}$ | 6.3 | $(5.35 \pm 0.15) \times 10^{-10}$ | 7.9 |

Example 25

A One Month Toxicity Study of Formulation "Paclitaxel-Sodium Salt of the Methyl Ester of N-all-Trans-Retinoyl Cysteic Acid-Sodium Salt of the Methyl Ester of N-13-Cis-Retinoyl Cysteic Acid (w/w/w 1:0.75:075)" in Rats The tested formulation was prepared by reconstitution in saline of freeze dried mixture of Paclitaxel-Sodium Salt of the Methyl Ester of N-all-trans-retinoyl Cysteic Acid-Sodium Salt of the Methyl Ester of N-13-cis-retinoyl Cysteic Acid (w/w/w 1:0.75:075). 80 Wistar rats (BRLHan:Wist@Mol (GALAS)), 40 males and 40 females, were divided into 4 groups, each of 10 males and 10 females. Tested formulations were administered by intravenous injection once weekly over 5 weeks. Group 1 received saline and acted as controls, Group 2 received 5 mg/kg of formulation of paclitaxel with polyoxyethylated castor oil (Taxol®), Group 3 received 5 mg/kg of the title formulation, and Group 4 received 10 mg/kg of the title formulation. Originally, the study was designed so that Group 2 would receive 10 mg/kg Taxol® as a direct comparison with Group 4, however, due to mortality, this dosage was reduced to 5 mg/kg such that a direct comparison with Group 3 was more appropriate. There were 8 deaths during the study. Seven rats received 10 mg/kg Taxol® died shortly after their first dose. Five of these rats were replaced with spares, and the dosage was reduced to 5 mg/kg. For females in Groups 2, 3 and 4 mean values for the red blood cell parameters (Hb, RBC and HT) were lower than for the controls. Although a similar change was not seen in the males, values for the red cell indices MCV in males of Group 2 were elevated. Mean values for white blood cells, particularly neutrophils, lymphocytes, eosinophils and in the males, monocytes in treated animals were lower than for controls. Mean serum bilirubin values for males in Group 4 and females in Group 2 and 4 were higher than for the controls. Bilirubin for females in Group 2 (Taxol®) was significantly higher than for the females in Group 3. Liver weight in males of Groups 2 and 4 was significantly lower than for the controls. Thymus weight for males and females in Group 4 and for the males in Group 2 was significantly lower than for the control. Relatively high incidence of minimal to slight lymphoid atrophy was recorded in the spleen, the mesenteric- and mandibular lymph node of Group 4. Low incidence of minimal to slight lymphoid atrophy was recorded in the spleen of Groups 2 and 3. The incidence lymphoid atrophy of the spleen was slightly higher in the Group 2 males. Low incidence of minimal to slight lymphoid atrophy was rerecorded in the mesenteric- and mandibular lymph nodes of Group 2. Minimal to slight increased cortical lymphocytolysis was recorded in all males of Group 2. In the mammary gland of the males from Groups 2 and 4, higher incidence of minimal multifocal decreased secretory vacuoles/hypoplasia of alveoli was recorded compared to control and Group 3. Increased incidence of mitotic figures/apoptotic bodies in the epithelial lining of the mammary gland was recorded in approximately half of the males of all treated groups.

This example demonstrates that nano-particle formulation "Paclitaxel-Sodium Salt of the Methyl Ester of N-all-trans-retinoyl Cysteic Acid-Sodium Salt of the Methyl Ester of N-13-cis-retinoyl Cysteic Acid (w/w/w 1:0.75:075)" has a lower toxicity as compared to identical concentrations of conventional formulation of paclitaxel with polyoxyethylated castor oil.

Example 26

Advantages of nano-particle formulation "Paclitaxel-Sodium Salt of the Methyl Ester of N-all-trans-retinoyl Cysteic Acid-Sodium Salt of the Methyl Ester of N-13-cis-retinoyl Cysteic Acid" as compared to conventional formulation of paclitaxel with polyoxyethylated castor oil (Taxol®). The main results and conclusions are summarized in the table 17 below.

Table 17. Comparison of paclitaxel formulations (results and set-up for the title formulation according to a study of treatment of 34 patients with histologically proven solid malignant tumour disease, for which no standard therapy was available or had failed; information about Taxol® in according to BMS PI Rev July 2007)

|  | Paclitaxel-Sodium Salt of the Methyl Ester of N-all-trans-retinoyl Cysteic Acid-Sodium Salt of the Methyl Ester of N-13-cis-retinoyl Cysteic Acid | Paclitaxel-polyoxyethylated castor oil |
| --- | --- | --- |
| Dose level/m$^2$ | 250 | 175 |
| Premedication with steroids, antiemetics and antihistamines | None | Yes |
| Anaphylaxis and severe hypersensitivity reactions | None (without premedication) | 5% (All patients received premedication) |
| Infusion time | 1 hour | 3 hours |

Although the invention has been described with regard to certain embodiments, including the best mode presently known to the inventors, it should be understood that various changes and modifications as would be obvious to one having the ordinary skill in this art may be made without departing from the scope of the invention as set forth in the claims appended hereto.

The invention claimed is:

1. A drug delivery system for administration of at least one pharmaceutically active substance having a solubility per se in water of less than about 100 μg/ml, said substance being in particulate form with an effective average particle size of less than about 100 nm, wherein
   the substance particles are essentially amorphous;
   the substance particles are entrapped in nanoparticles formed of a sodium salt of the methyl ester of N-all-trans-retinoyl cysteic acid, sodium salt of methyl ester of N-13-cis-retinoyl cysteic acid, or a combination thereof;
   the weight-to-weight ratio of said sodium salt of methyl ester of N-all-trans-retinoyl cysteic acid, sodium salt of methyl ester of N-13-cis-retinoyl cysteic acid, or a combination thereof, to said substance is in the range from about 0.5:1 to about 20:1; and
   said substance is an immunosuppressant chosen from among ciclosporin, sirolimus, tacrolimus and derivatives thereof.

2. A drug delivery system according to claim 1, wherein the weight-to-weight ratio of said sodium salt of the methyl ester of N-all-trans-retinoyl cysteic acid, sodium salt of the methyl ester of N-13-cis-retinoyl cysteic acid, or a combination thereof, to said substance is in the range from about 1:1 to about 10:1.

3. A drug delivery system according to claim 1, for use in post-allogeneic organ transplant.

4. A pharmaceutical composition comprising a pharmaceutically acceptable carrier and the drug delivery system according to claim 1.

5. A pharmaceutical composition according to claim 4 in the form of an aqueous solution, a gel, a cream, an ointment, a tablet, a capsule, or a softgel.

6. A method for post-allogeneic organ transplant, wherein a pharmaceutical composition comprising a pharmaceutically acceptable carrier and a drug delivery system according to claim 1 is administered in a therapeutically effective amount to a patient in need of such treatment.

7. A method for post-allogeneic organ transplant, wherein the drug delivery system according to claim 1 is administered in a therapeutically effective amount to a patient in need of such treatment.

* * * * *